(12) United States Patent
Hochberg

(10) Patent No.: US 8,552,061 B2
(45) Date of Patent: Oct. 8, 2013

(54) LOCALLY ACTIVE "SOFT" ANTIANDROGENS

(75) Inventor: Richard Hochberg, Guilford, CT (US)

(73) Assignee: Yale University, New Haven, CT (US)

( * ) Notice: Subject to any disclaimer, the term of this patent is extended or adjusted under 35 U.S.C. 154(b) by 620 days.

(21) Appl. No.: 12/450,862

(22) PCT Filed: May 2, 2008

(86) PCT No.: PCT/US2008/005632
§ 371 (c)(1),
(2), (4) Date: Mar. 19, 2010

(87) PCT Pub. No.: WO2008/137038
PCT Pub. Date: Nov. 13, 2008

(65) Prior Publication Data
US 2010/0184735 A1    Jul. 22, 2010

Related U.S. Application Data

(60) Provisional application No. 60/927,427, filed on May 3, 2007.

(51) Int. Cl.
*A61K 31/216* (2006.01)
*C07C 205/06* (2006.01)

(52) U.S. Cl.
USPC .......................................... 514/542; 560/22

(58) Field of Classification Search
USPC ............................................ 560/22; 514/542
See application file for complete search history.

(56) References Cited

U.S. PATENT DOCUMENTS

| | | | |
|---|---|---|---|
| 4,396,614 | A | 8/1983 | Nedelec et al. |
| 5,364,847 | A | 11/1994 | Labrie et al. |
| 5,610,150 | A | 3/1997 | Labrie |
| 6,147,213 | A | 11/2000 | Poli et al. |
| 2005/0026889 | A1 | 2/2005 | Ajani et al. |

FOREIGN PATENT DOCUMENTS

| | | |
|---|---|---|
| EP | 0055170 | 10/1984 |
| EP | 1219631 | 7/2002 |
| GB | 1446084 | 8/1976 |
| JP | H49-81332 | 8/1974 |
| JP | S57-163399 | 10/1982 |
| JP | H6-273417 | 9/1994 |
| WO | WO 00/31112 | 6/2000 |
| WO | WO 01/14406 | 3/2001 |

OTHER PUBLICATIONS

Bruchovsky N, Wilson JD 1968 The intranuclear binding of testosterone and 5-alpha-androstan-17-beta-ol-3-one by rat prostate. J Biol.Chem 243:5953-5960.

Imperato-McGinley J, Guerrero L, Gautier T, Peterson RE 1974 Steroid 5alpha-reductase deficiency in man: an inherited form of male pseudohermaphroditism. Science 186:1213-1215.

Cleland WH, Mendelson CR, Simpson ER 1985 Effects of aging and obesity on aromatase activity of human adipose cells. J.Clin. Endocrinol.Metab. 60:174-177.

Smith EP, Boyd J, Frank GR, Takahashi H, Cohen RM, Specker B, Williams TC, Lubahn DB, Korach KS 1994 Estrogen resistance caused by a mutation in the estrogen-receptor gene in a man. N.EngI. J.Med. 331:1056-1061.

Snyder PJ 2001 The role of androgens in women. J.Clin.Endocrinol. Metab 86:1006-1007.

(Continued)

*Primary Examiner* — Barbara P Badio
(74) *Attorney, Agent, or Firm* — Henry D. Coleman; R. Neil Sudol

(57) ABSTRACT

The present invention relates to antiandrogenic compounds which may be administered for the treatment of androgen excess in the skin and by way of consequence, the treatment of acne, baldness or hirsuitism in subject or patient. These compounds have the general chemical structure (I, II, III or IV).

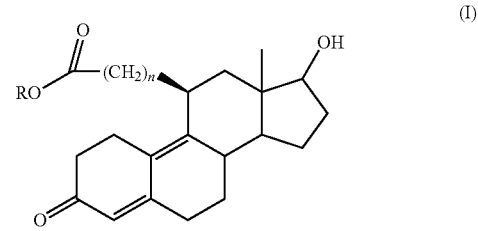

(I)

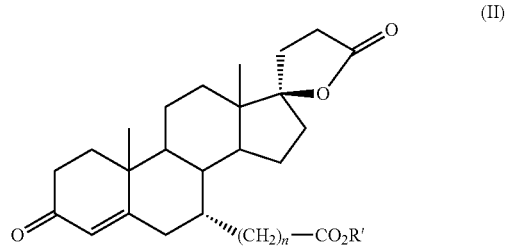

(II)

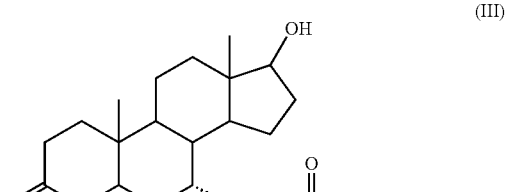

(III)

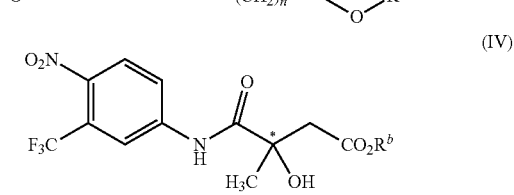

(IV)

37 Claims, 2 Drawing Sheets

(56) References Cited

OTHER PUBLICATIONS

Figure 1:
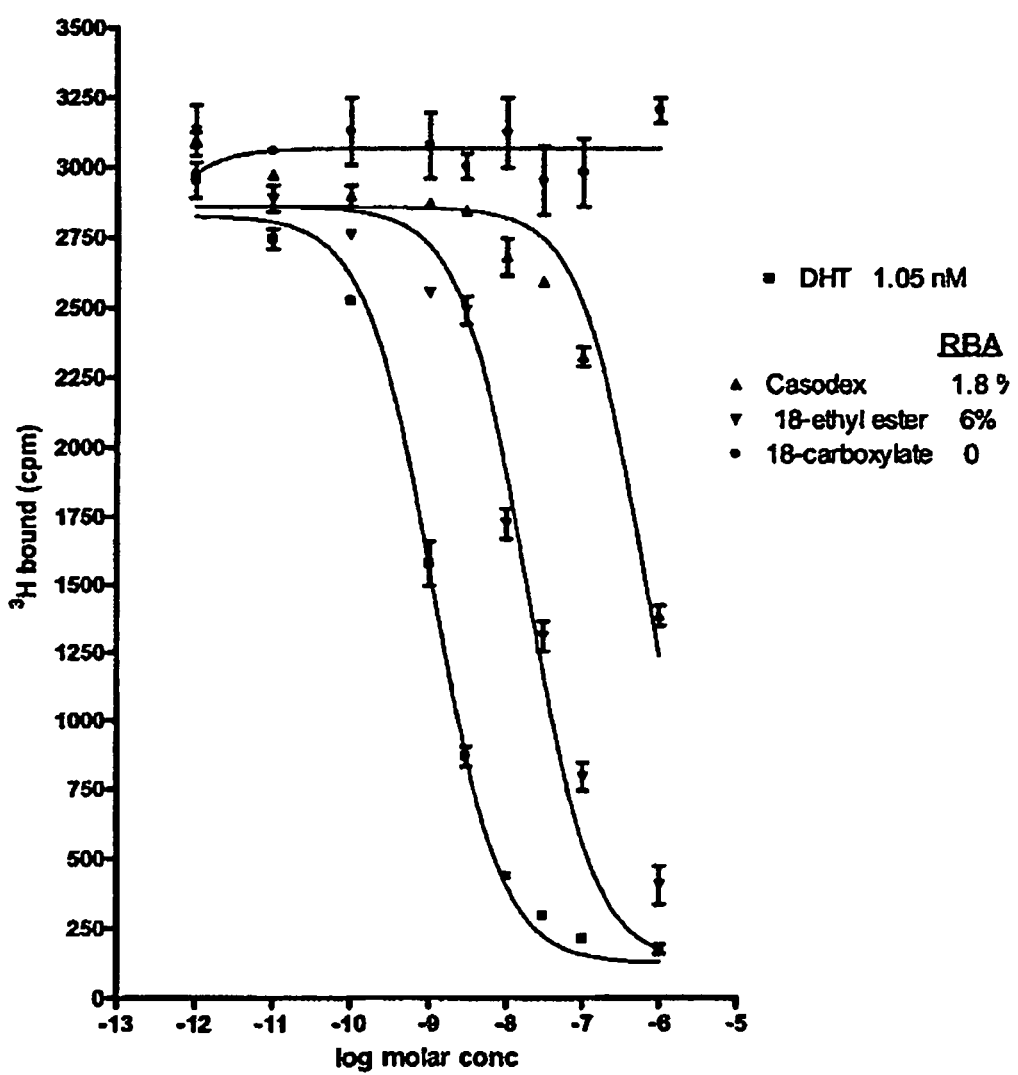

Speiser PW, New MI 1987 Genotype and hormonal phenotype in nonclassical 21-hydroxylase deficiency. J Clin.Endocrinol.Metab 64:86-91.

Knochenhauer ES, Key TJ, Kahsar-Miller M, Waggoner W, Boots LR, Azziz R 1998 Prevalence of the polycystic ovary syndrome in unselected black and white women of the southeastern United States: a prospective study. J Clin.Endocrinol.Metab 83:3078-3082.

Avgerinos PC, Cutler GB, Jr., Tsokos GC, Gold PW, Feuillan P, Gallucci WT, Pillemer SR, Loriaux DL, Chrousos GP 1987 Dissociation between cortisol and adrenal androgen secretion in patients receiving alternate day prednisone therapy. J Clin.Endocrinol.Metab 65:24-29.

Cumming DC, Yang JC, Rebar RW, Yen SS 1982 Treatment of hirsutism with spironolactone. JAMA 247:1295-1298.

Cusan L, Dupont A, Gomez JL, Tremblay RR, Labrie F 1994 Comparison of flutamide and spironolactone in the treatment of hirsutism: a randomized controlled trial. Fertil.Steril. 61:281-287.

Rittmaster RS 1994 Finasteride. N.Engl.J Med 330:120-125.

McConnell JD, Wilson JD, George FW, Geller J, Pappas F, Stoner E 1992 Finasteride, an inhibitor of 5 alpha-reductase, suppresses prostatic dihydrotestosterone in men with benign prostatic hyperplasia. J Clin.Endocrinol.Metab 74:505-508.

Rosner W 2004 Proscar and propecia—a therapeutic perspective. J Clin.Endocrinol.Metab 89:3096-3098.

Davis S 1999 Androgen replacement in women: a commentary. J Clin.Endocrinol.Metab 84:1886-1891.

Youngkin EQ 1990 Estrogen replacement therapy and the estraderm transdermal system. Nurse Pract. 15:19-26, 31.

Fant RV, Henningfield JE, Shiffman S, Strahs KR, Reitberg DP 2000 A pharmacokinetic crossover study to compare the absorption characteristics of three transdermal nicotine patches. Pharmacol. Biochem . Behav. 67:479-482.

Bodor N 1982 Designing safer drugs based on the soft drug approach. Trends Pharmac Sci 3:53-56.

Graffner-Nordberg M, Sjodin K, Tunek A, Hallberg A 1998 Synthesis and enzymatic hydrolysis of esters, constituting simple models of soft drugs. Chem Pharm Bull (Tokyo) 46:591-601.

Lee HJ, Bradlow HL, Moran MC, Sherman MR 1981 Binding of glucocorticoid 21-OIC acids and esters to molybdate-stabilized hepatic receptors. J.Ster.Biochem. 14:1325-1335.

Lee HJ, Soliman MRI 1982 Anti-inflammatory steroids without pituitary adrenal suppression. Science 215:989-991.

Laurent H, Gerhards E, Wiechert R 1975 New biologically active pregnan-21-oic acid esters. J Steroid Biochem 6:185-192.

Druzgala P, Hochhaus G, Bodor N 1991 Soft drugs—10. Blanching activity and receptor binding affinity of a new type of glucocorticoid: loteprednol etabonate. J Steroid Biochem Mol Biol 38:149-154.

Szelenyi I, Hochhaus G, Heer S, Kusters S, Marx D, Poppe H, Engel J 2000 Loteprednol etabonate: a soft steroid for the treatment of allergic diseases of the airways. Drugs Today (Barc.) 36:313-320.

Sarrel PM 1990 Sexuality and Menopause. Obstetrics and Gynecology 75:26S-30S.

Writing Group for the Women's Health Initiative Investigators 2002 Risks and benefits of estrogen plus progestin in healthy postmenopausal women: principal results From the Women's Health Initiative randomized controlled trial. JAMA 288:321-333.

Schiff I, Tulchinsky D, Ryan KJ 1977 Vaginal absorption of estrone and 1713-estradiol. Fertility and Sterility 28:1063-1066.

Rigg LA, Hermann H, Yen SSC 1978 Absorption of estrogens from vaginal creams. N.Engl.J.Med. 298:195-197.

Martin PL, Yen SSC, Burnier AM, Hermann H 1979 Systemic absorption and sustained effects of vaginal estrogen creams. JAMA 242:2699-2700.

Schiff I, Tulchinsky D, Ryan KJ, Kadner S, Levitz M 1980 Plasma estriol and its conjugates following oral and vaginal administration of estriol to postmenopausal women: correlations with gonadotropin levels. Am.J.Obstet.Gynecol. 138:1137-1141.

Bucourt R, Vignau M, Torelli V 1978 New biospecific adsorbents for the purification of estradiol receptor. J.Biol.Chem 253:8221-8228.

Labaree DC, Reynolds TY, Hochberg RB 2001 Estradiol-16a-carboxylic Acid Esters as Locally Active Estrogens. J Med Chem 44:1802-1814.

Labaree DC, Zhang J, Harris HA, O'Connor C, Reynolds TY, Hochberg RB 2003 The Synthesis and Evaluation of B-, C-, and D-ring Substituted Estradiol Carboxylic Acid Esters as Locally Active Estrogens. J Med Chem 46:1886-1904.

Zhang J, Labaree DC, Mor G, Hochberg RB 2004 Estrogen to Antiestrogen with a Single Methylene Group Resulting in an Unusual Steroidal SERM. J.Clin.Endocrinol.Metab. 89:3527-3535.

Zhang JX, Labaree DC, Hochberg RB 2005 Nonpolar and short sidechain groups at C-11 of estradiol result in antiestrogens. J Med Chem 48:1428-1447.

Muddana SS, Price AM, MacBride MM, Peterson BR 2004 1113-Alkyl-49-19-nortestosterone derivatives: high-affinity ligands and potent partial agonists of the androgen receptor. Journal of Medicinal Chemistry 47:4985-4988.

Centrella M, McCarthy TL, Wei-Zhong C, Labaree DC, Hochberg RB 2004 Estren (4-Estren-3-a,17(3-diol) Is a prohormone that can regulate estrogen- and androgen-like effects through the androgen receptor. MoI.Endocrinol. 18:1120-1130.

He Y, Yin D, Perera M, Kirkovsky L, Stourman N, Li W, Dalton JT, Miller DD 2002 Novel nonsteroidal ligands with high binding affinity and potent functional activity for the androgen receptor. Eur.J Med Chem 37:619-634.

Nirde P, Terouanne B, Gallais N, Sultan C, Auzou G 2001 Antimineralocorticoid 11 b-substituted spirolactones exhibit androgen receptor agonistic activity: a structure function study. Molecular Pharmacology 59:1307-1313.

Pannatier A, Testa B, Etter J 1981 Enzymatic hydrolysis by mouse skin homogenates: structure-metabolism relationships of para-nitrobenzoate esters. International Journal of Pharmaceutics 8:167-174.

Hanson RN, Napolitano E, Fiaschi R, Onan KD 1990 Synthesis and estrogen receptor binding of novel 1113-substituted estra-1,3,5(10)-triene-3,17(3-diols. J.Med.Chem. 33:3155-3160.

Corey EJ, Schmidt G 1979 Useful procedures for the oxidation of alcohols involving pyridinium dichromate in aprotic media. Tetrahedron Letters :399-402.

Guindon Y, Yoakim C, Morton HE 1983 Cleavage of carbon-oxygen bonds. Dimethylboron bromide. A new reagent for ether cleavage. Tetrahedron Letters 24:2969-2972.

Guindon Y, Yoakim C, Morton HE 1984 Dimethylboron bromide and diphenylboron bromide: cleavage of acetals and ketals. J.Org.Chem. 49:3912-3920.

Monti H, Leandri G, Klos-Ringuet M, Corriol C 1983 An efficient deprotective method for allylic alcohols protected as methoxyethoxymethyl (MEM) and methoxymethyl (MOM) ethers. Synthetic Communications 13:1021-1026.

Sogani PC, Whitmore WF, Jr. 1988 Flutamide and other antiandrogens in the treatment of advanced prostatic carcinoma. Cancer Treat.Res. 39:131-145.

Morris JJ, Hughes LR, Glen AT, Taylor PJ 1991 Non-steroidal antiandrogens. Design of novel compounds based on an infrared study of the dominant conformation and hydrogen-bonding properties of a series of anilide antiandrogens. Journal of Medicinal Chemistry 34:447-455.

Tucker H, Crook JW, Chesterson GJ 1988 Nonsteroidal antiandrogens. Synthesis and structure-activity relationships of 3-substituted derivatives of 2-hydroxypropionanilides. Journal of Medicinal Chemistry 31:954-959.

Yin D, He Y, Perera MA, Hong SS, Marhefka C, Stourman N, Kirkovsky L, Miller DD, Dalton JT 2003 Key structural features of nonsteroidal ligands for binding and activation of the androgen receptor. Molecular Pharmacology 63:211-223.

Seligson AL, Campion BK, Brown JW, Terry RC, Kucerova R, Bienova M, Hajduch M, Sovak M 2003 Development of fluridil, a topical suppressor of the androgen receptor in androgenetic alopecia. Drug Dev.Res. 59:292-306.

(56) References Cited

OTHER PUBLICATIONS

Poujol N, Wurtz JM, Tahiri B, Lumbroso S, Nicolas JC, Moras D, Sultan C 2000 Specific recognition of androgens by their nuclear receptor. A structure-function study. J Biol.Chem 275:24022-24031.
Whitesell JK, Nabona K, Deyo D 1989 Observations on the reactions of chiral pyruvates. Synthesis of (−)- and (+)-citramalic acid. J.Org. Chem. 54:2258-2260.
Wuensch B, Diekmann H, Hoefner G 1993 Homochiral 2,4-disubstituted 1,3-dioxanes from (S)-(−)-malic acid: stereoselective synthesis and investigation of the NMDA receptor affinity of all four stereoisomers. Liebigs Annalen der Chemie :1273-1278.
Bonher TG, Bourne EJ, McNally S 1960 Dealkylation and deacylation of carbohydrate derivatives with boron trichloride and boron tribromide. Journal of the Chemical Society, Abstracts :2929-2934.
Steelman SL, Brooks JR, Morgan ER, Patanelli DJ 1969 Anti-androgenic activity of spironolactone. Steroids 14:449-450.
Sobbrio GA, Granata A, Panacea A, Trimarchi F 1989 Effectiveness of short term canrenone treatment in idiopathic hirsutism. Minerva Endocrinol. 14:105-108.
Cutler GB, Jr., Sauer MA, Loriaux DL 1979 SC 25152: a potent mineralocorticoid antagonist with decreased antiandrogenic activity relative to spironolactone. J Pharmacol.Exp.Ther. 209:144-146.
Nickisch K, Laurent H 1988 Stereoselective synthesis of 7a-allyl- and 7a-propylsteroids. Tetrahedron Letters 29:1533-1536.
Solo AJ, Caroli C, Darby MV, McKaya T, Slaunwhite WD, Hebborn P 1982 7a-Alkyltestosterone derivatives: synthesis and activity as androgens and as aromatase inhibitors. Steroids 40:603-614.
Choe YS, Lidstrom PJ, Chi DY, Bonasera TA, Welch MJ, Katzenellenbogen JA 1995 Synthesis of 11 [3-[18F]fluoro-5a-dihydrotestosterone and 11 [3-[18F]fluoro-19-nor-5a-dihydrotestosterone: Preparation via halofluorination-reduction, receptor binding, and tissue distribution. J.Med.Chem. 38:816-825.
Wang WB, Roskamp EJ 1992 Tin(11) amides: new reagents for the conversion of esters to amides. J.Org.Chem. 57:6101-6103.
Mukaiyama T, Usui M, Shimada E, Saigo K 1975 Convenient method for the synthesis of carboxylic esters. Chemistry Letters :1045-1048.
Hoyte RM, Borderon K, Bryson K, Allen R, Hochberg RB, Brown TJ 1994 Synthesis and evaluation of 7a-lodo-5a-dihydrotestosterone as a potential radioligand for androgen receptor. J.Med.Chem. 37:1224-1230.
Labaree DC, Hoyte RM, Nazareth LV, Weigel NL, Hochberg RB 1999 7a-iodo and fluoro steroids as androgen receptor mediated imaging agents. J.Med.Chem. 42:2021-2034.
Chang CS, Kokontis J, Liao ST 1988 Molecular cloning of human and rat complementary DNA encoding androgen receptors. Science 240:324-326.
McCarthy TL, Chang WZ, Liu Y, Centrella M 2003 Runx2 integrates estrogen activity in osteoblasts. J Biol.Chem 278:43121-43129.
Lindner W 1980 N-chloromethyl-4-nitrophthalimide as derivatization reagents for high-performance liquid chromatography. Journal of Chromatography 198:367-372.
Lund-Pero M, Jeppson B, Arneklo-Nobin B, Sjogren H-O, Holmgren K, Pero RW 1994 Nonspecific steroidal esterase activity and distribution in human and other mammalian tissues. Clinica Chimica Acta 224:9-20.
Corvol P, Claire M, Oblin ME, Geering K, Rossier B 1981 Mechanism of the antimineralocorticoid effects of spirolactones. Kidney Int. 20:1-6.
Brown TJ, MacLusk r NJ, Toran-Allerand CD, Zielinski JE, Hochberg RB 1989 Characterization of 11 [3-methoxy-16a-[' 51]iodoestradiol binding: neuronal localization of estrogen binding sites in the developing rat brain. Endocrinology 124:2074-2088.
Moguilewsky M, Raynaud JP 1980 Evidence for a specific mineralocorticoid receptor in rat pituitary and brain. J.Steroid Biochem. 12:309-314.
Lopez S, Miyashita Y, Simons SS, Jr. 1990 Structurally based, selective interaction of arsenite with steroid receptors. J Biol.Chem 265:16039-16042.

Hoyte RM, Labaree DC, Fede JM, Harris C, Hochberg RB 1998 Iodinated and fluorinated steroid 2'-aryl-[3,2-c] pyrazoles as potential glucocorticoid receptor imaging agents. Steroids 63:595-602.
Petrazzuoli M, Pahuja SL, Larner TM, Hochberg RB 1990 Biological activity of the fatty acid ester metabolites of corticoids. Endocrinology 127:555-559.
Quinkler M, Meyer B, Bumke-Vogt C, Grossmann C, Gruber U, Oelkers W, Diederich S, Bahr V 2002 Agonistic and antagonistic properties of progesterone metabolites at the human mineralocorticoid receptor. Eur.J Endocrinol. 146:789-799.
Chambers SK, Ivins CM, Kacinski BM, Hochberg RB 2004 An unexpected effect of glucocorticoids on stimulation of c-fms proto-oncogene exprssion in choriocarcinoma cells expressing little glucocorticoid receptor. Am J Obstet Gynecol 190:974-985.
Arriza JL, Weinberger C, Cerelli G, Glaser TM, Handelin BL, Housman DE, Evans RM 1987 Cloning of human mineralocorticoid receptor complementary DNA: Structural and functional kinship with the glucocorticoid receptor. Science 237:268-275.
Littlefield BA, Cidlowski NB, Cidlowski JA 1980 Modulation of glucocorticoid effects and steroid receptor binding in butyrate-treated HeLa S3 cells. Arch.Biochem.Biophys. 201:174-184.
Jausons-Loffreda N, Balaguer P, Auzou G, Pons M 1994 Development of specific bioluminescent in vitro assays for selecting potential antimineralocorticoids. J Steroid Biochem.Mol.Biol. 49:31-38.
Littlefield BA, Gurpide E, Markiewicz L, McKinley B, Hochberg RB 1990 A simple and sensitive microtiter plate estrogen bioassay based on stimulation of alkaline phosphatase in Ishikawa cells: Estrogenic action of A5 adrenal steroids. Endocrinology 127:2757-2762.
Luderschmidt C, Eiermann W, Jawny J, Bidlingmaier F, Ring J 1984 17 alpha-Propylmesterolone (SH 434): an antiandrogenic sebosuppressive substance not influencing circulating testosterone concentrations. Experimental studies in Syrian hamsters. Naunyn Schmiedebergs Arch. Pharmacol. 328:214-218.
Matias JR, Malloy VL, Orentreich N 1988 Synergistic antiandrogenic effects of topical combinations of 5 alpha-reductase and androgen receptor inhibitors in the hamster sebaceous glands. J Invest Dermatol. 91:429-433.
Gaunt R, Gisoldi E, Smith N 1971 Refractoriness to renal effects of aldosterone in the golden hamster. Endocrinology 89:63-69.
Sekihara H, Yazaki Y 1993 5 alpha-Dihydro-1 1-deoxycorticosterone as a mineralocorticoid agonist and antagonist: evidence for a weak mineralocorticoid as an antagonist of potent mineralocorticoids. J Steroid Biochem.Mol.Biol. 45:235-238.
Rosner W, Hochberg RB 1972 Corticosteroid-binding globulin in the rat: Isolation and studies of its influence on cortisol action in vivo. Endocrinology 91:626-632.
Ye F, Imamura K, Imanishi N, Rhodes L, Uno H 1997 Effects of topical antiandrogen and 5-alpha-reductase inhibitors on sebaceous glands in male fuzzy rats. Skin Pharmacol. 10:288-297.
Marit GB, Young SM, Hadick CL 1995 Anatomic and physiologic characterization of the WF/PmWp-"fz" (fuzzy) rat. Lab Anim Sci 45:184-190.
Menard RH, Guenthner TM, Kon H, Gillette JR 1979 Studies on the destruction of adrenal and testicular cytochrome P-450 by spironolactone. Requirement for the 7alpha-thio group and evidence for the loss of the heme and apoproteins of cytochrome P-450. J Biol.Chem 254:1726-1733.
Rey FO, Valterio C, Locatelli L, Ramelet AA, Felber JP 1988 Lack of endocrine systemic side effects after topical application of spironolactone in man. J.Endocrinol.Invest 11:273-278.
Borg W, Shackleton CHL, Pahuja SL, Hochberg RB 1995 Endogenous Long-Lived Esters of Testosterone in the Rat. Proc.Natl. Acad.Sci.USA 92:1545-1549.
Tucker H et al.; Nonsteroidal antiandrogens. Synthesis and structure-activity relationshhips of 3-substituted derivatives of 2-hydroxypropionanilides; Journal of Medicinal Chemistry 1988; 31:954-959.
Seligson AL et al.; Development of fluridil, a topical suppressor of the androgen receptor in androgenetic alopecia; Drug Dev.Res. 2003; 59:292-306.

LOCALLY ACTIVE "SOFT" ANTIANDROGENS

RELATED APPLICATIONS AND GRANT SUPPORT

The present application claims the basis of priority from U.S. provisional application Ser. No. 60/927,427, filed May 3, 2007, of identical title, the entire contents of which is incorporated by reference herein.

The subject matter of this application was supported by NIH grant nos. NIH R01 CA-37799 and HL-61432. Consequently, the United States government retains certain rights in the invention.

FIELD OF THE INVENTION

The present invention relates to antiandrogenic compounds which may be administered for the treatment of androgen excess in the skin and by way of consequence, the treatment of acne, baldness or hirsuitism in subject or patient.

BACKGROUND OF THE INVENTION

Androgen action is the result of a physiologically complex sequence that is ultimately controlled by opposing pathways of steroid biosynthesis and catabolism. For decades it was assumed that the testicular secretory product, testosterone, is the predominant androgen, but now it is widely recognized that this $C_{19}$-steroid is an androgenic precursor, the product of incomplete steroidogenic pathways that lead to the ultimate hormonal signals. An array of physiological and pathological studies have shown that testosterone, secreted by the testes and ovary (or peripherally synthesized from androstenedione secreted by the ovary) and in primates, the adrenal, is converted by target tissues into the active androgen, 5a-dihydrotestosterone (DHT)(1,2). The 5α-reductase type 2 enzyme produces the active androgen by converting testosterone, a $\Delta^4$-3-ketone, into the corresponding 5a-reduced steroid. Circulating testosterone and androstenedione also serve as precursors of the estrogens through their conversion to estradiol ($E_2$) and estrone by the aromatase enzyme present in many tissues, especially fat (3). Thus, regardless of gender, these secreted $C_{19}$-$\Delta^4$-3-ketosteroids are converted peripherally into divergent signals for 2 different members of the steroid hormone nuclear receptor family. Because of ovarian secretion, estrogens are generally associated with females, and because of testicular secretion, androgens are associated with males. In actuality, each plays a key role in both sexes. As one example, the requirement for estrogens in bone maturation and mineralization in males was demonstrated in an estrogen resistant man having a mutated estrogen receptor (ER) alpha (4). Androgens are known to play important physiological roles in women, and an androgen deficiency syndrome in women is recognized as an important clinical syndrome, involving defects in bone remodeling, sexual function and quality of life (5).

While there are obvious important physiological requirements for androgens in both men and women, there are a number of syndromes in which pathological overproduction of androgens occurs, either in steroidogenic organs or in target tissues. Perhaps the best known is the adrenogenital syndrome, principally the 21-hydroxylase deficiency, which leads to an overproduction of androgen from the adrenal. Some forms of this syndrome are expressed only subtlety (non-classical) leading to milder forms of late onset androgenization (hirsutism, acne) (6). The most prevalent disorder of androgen excess in women is polycystic ovarian syndrome (PCOS) which affects over 5% of reproductive age women (7). Pharmacological intervention varies according to the disorder. The adrenogenital syndrome is treated with dexamethasone which reduces ACTH secretion thereby controlling adrenal androgen synthesis (8). In women, depending upon the source of androgen, hyperandrogenism often responds to oral contraceptives which reduce LH and thereby reduces the stimulation of ovarian androgen secretion, and the estrogenic component of the contraceptive increases sex hormone binding globulin levels which decreases bio-available testosterone. Significant hirsutism is often treated with antiandrogens such as cyproterone acetate, spironolactone or flutamide: cyproterone acetate is a progestin and an antiandrogen that lowers gonadotrophins thus circulating androgens and it inhibits androgen action at the level of the receptor (9); spironolactone is a mineralocorticoid antagonist that is also an androgen receptor antagonist; flutamide is a pure androgen antagonist (10). In addition to antiandrogens, finasteride, the specific inhibitor of the "metabolic activation" of testosterone, is available (11). This compound acts on the 5areductase enzyme type 2, blocking the peripheral conversion of testosterone to DHT in most androgen target organs.

While the availability of this wide array of therapeutic agents makes it possible to treat most forms of hyperandrogenic syndromes, this systemic therapy is not without its pitfalls. For example, in men, antiandrogen therapy with finasteride (Proscar) is common in the treatment of benign prostatic hypertrophy, to prevent progression to prostate cancer. While Proscar is efficacious in decreasing the incidence of low grade prostate cancer, the incidence of high-grade prostate cancers actually increases (12). This called into question the use of antiandrogen therapy to prevent a disorder as serious as prostate cancer. Also questioned is the use of finasteride for the treatment of a much less serious problem; Finasteride, in a formulation called Propecia, is also employed for the treatment baldness. Although Propecia delivers a lower dose of Finasteride than Proscar, it has the same effect on the levels of DHT and testosterone in plasma and prostate (13). This has raised the possibility that this large number of young men who would take Propecia for most of their lives for the treatment of alopecia, might be at increased risk of high-grade prostate cancer (14). As discussed above, interfering with androgen action has clinical ramifications for women as well as men since women also have androgen dependent processes. This is illustrated by androgen replacement therapy becoming a recommended treatment for women with low androgen levels (15). Thus, producing an androgen deficiency syndrome by pharmacological inhibition of androgen action carries significant health risks for both men and women.

While it is apparent that the inhibition of androgen action to treat acne and baldness in men and women, and hirsutism in women, is efficacious, it can carry serious risks. However, this risk may not be necessary since all of these maladies are localized to the skin, an organ that can be treated directly rather than systemically. Systemic androgenic antagonism is not necessary if the antagonist can be applied to, and contained within the skin. Although the skin is an organ that responds to topically applied drugs, it is also permeable to a wide variety of drugs. Thus, many drugs, for example, estrogens, and nicotine, that are applied with skin patches enter the body, circulate in the blood and act systemically (16,17). An antiandrogen developed to act locally, solely within the skin, without systemic action, would alleviate this problem. The design and synthesis of a locally active androgen antagonist to be applied to the skin to treat acne, alopecia, seborrhea, as well as hirsutism is the subject of this application.

OBJECTS OF THE INVENTION

It is an object of the invention to provide novel compounds and pharmaceutical compositions for use in treating acne, alopecia (baldness), seborrhea (especially in women) and hirsutism.

It is yet another object of the invention to provide methods for treating one or more of acne, baldness, seborrhea and hirsutism utilizing compounds and compositions according to the present invention.

It is still a further object of the present invention to provide novel compounds and compositions which may be used in a prophylactic manner to reduce the likelihood of the occurrence or recurrence of acne, baldness, seborrhea and hirsutism.

Any one of these and/or other objects of the present invention may be readily gleaned from the description of the invention which follows.

BRIEF DESCRIPTION OF THE INVENTION

FIG. 1 shows the androgen receptor (AR) binding of Compound 18-ester & its corresponding carboxylate. The antiandrogenic potential of compound 18 acid and ethyl ester in comparison to the classical non-steroidal antiandrogen bicalutamide, were characterized by determining 1): their affinity for the AR in rat prostate cytosol (see the methods section); measuring their competition for the binding of [$^3$H] 5a-DHT. Cytosol was incubated with 1 nM [$^3$H]5a-DHT overnight in the presence of the 3 compounds and DHT. Afterwards the free steroid was adsorbed with charcoal and the receptor bound radioactivity measured by counting. As can be seen in this figure, compound 18-ethyl ester competes for binding to AR with a RBA of about 6%, this compares to −2% for bicalutamide (casodex). The results show that the esterified compound exhibits significant antiandrogenic activity, whereas the corresponding carboxylate does not bind to the androgen receptor, leading one to conclude that the ester is the active species, whereas deesterification to the free carboxylate results in inactivity.

Figure 2:
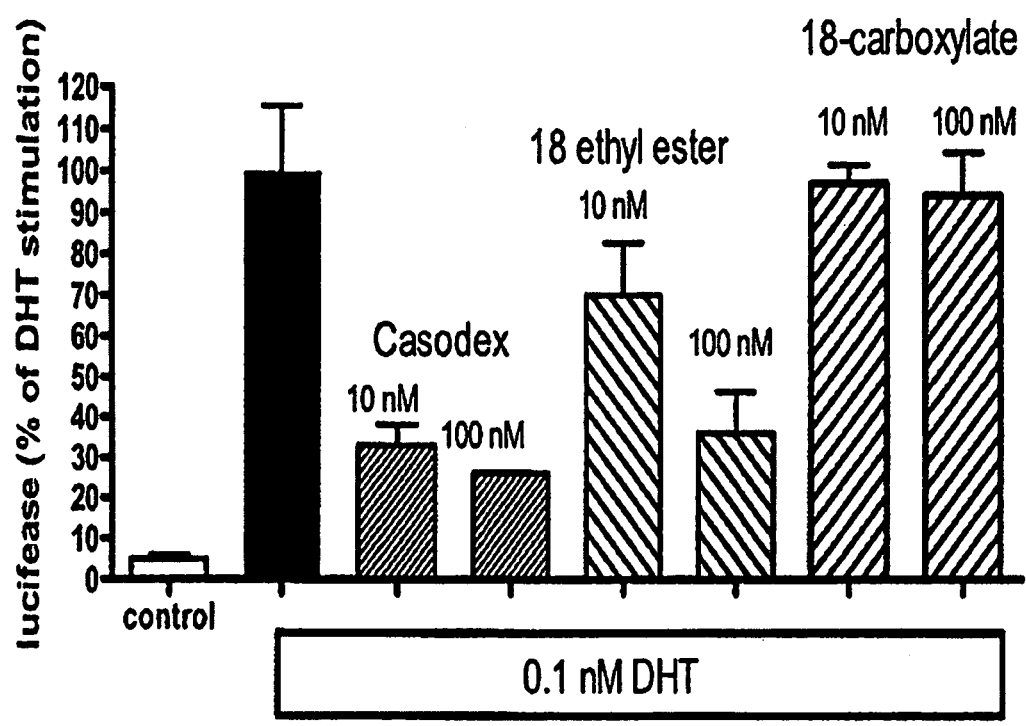

FIG. 2 shows the effect of compound 18-ethyl ester on the DHT Stimulation of cells tranfected with AR and an ARE—Luciferase reporter gene. The antiandrogenic action of compound 18-ester and carboxylate was measured in primary osteoblast cultures derived from fetal rat parietal bones transfected with human AR and an ARE-luciferase linked reporter gene as previously reported. Centrella, et al., *Mol. Endocrinol.*, 18:1120-1130, 2004. The cells were treated for with DHT 0.1 nM or vehicle (DMSO 0.1%) alone control, or DHT with one of the following: 18-ethyl ester, 18-carboxylate or casodex (bicalutamide). The non-steroidal analogs were added simultaneously with DHT. Twentyfour hours later the cells were tested for luciferase activity.

BRIEF DESCRIPTION OF THE INVENTION

The present invention relates to compounds according to the chemical structure:

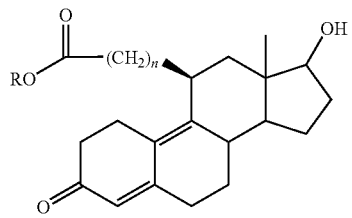

Where n is 1, 2 or 3 (preferably 1 or 2); and
R is an optionally substituted (with a $C_1$-$C_3$ alkyl or fluoroalkyl) $C_4$-$C_{10}$ group, wherein R is a $C_5$-$C_{10}$ alkyl group (preferably an unsubstituted straight-chained alkyl group) when n=1 and R is an optionally substituted (with a $C_1$-$C_3$ alkyl or fluoroalkyl) $C_4$-$C_{10}$ alkyl group, preferably an unsubstituted straight-chained alkyl group when n=2, or

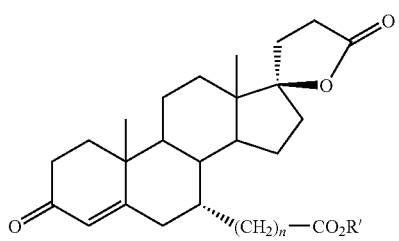

Where n is 1, 2 or 3 (preferably 1 or 2) and R' is an optionally substituted (with a $C_1$-$C_3$ alkyl or fluoroalkyl group) $C_1$-$C_5$ alkyl group; or

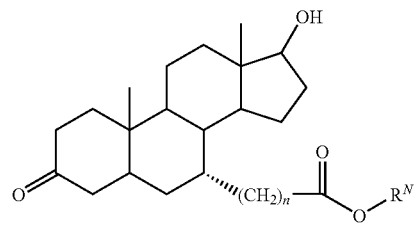

Where n is 1, 2 or 3 (preferably 1 or 2);
$R^N$ is a

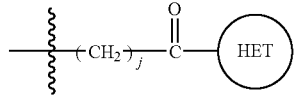

group or a

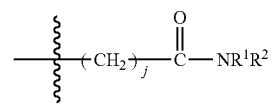

group;
j is 2, 3 or 4 (preferably 2 or 3, preferably 3) and

is a 5 or 6 membered heterocyclic group containing at least one nitrogen atom bonded to the carbonyl group, optionally substituted with from 1-3 methyl groups or halogen groups (F, Cl, Br, I, preferably F) and is preferably piperidine, piperazine or morpholine (preferably piperidine).

$R^1$ and $R^2$ are each independently H, or a $C_1$-$C_4$ alkyl group, or

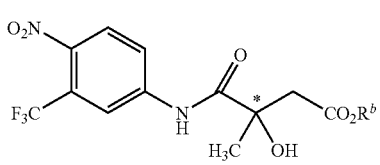

IV

Where * signifies a chiral center and $R^b$ is a $C_1$-$C_6$ optionally substituted (with $C_1$-$C_3$ alkyl or fluoroalkyl) alkyl group, preferably an ethyl group.

In certain preferred aspects of the present invention related to the non-steroidal compound above, the compound is:

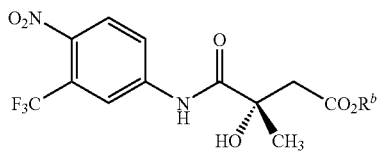

Where $R^b$ is a $C_1$-$C_6$ optionally substituted (with $C_1$-$C_3$ alkyl or fluoroalkyl) alkyl group, preferably an ethyl group.

The present invention also relates to pharmaceutical compositions according to the present invention comprising an effective amount of at least one compound as described above in combination with a pharmaceutically acceptable carrier, additive or excipient. Preferably, pharmaceutical compositions according to the present invention are formulated in topical dosage form for administration to the patient.

In another aspect of the present invention, a therapeutic treatment comprises administering one or more of the active compounds according to the present invention to a patient in need of therapy for the treatment of acne, alopecia (baldness), seborrhea or hirsutism. Prophylactic aspects of the present invention are also contemplated by the present invention and incorporated under general treatment methods. A particularly preferred prophylactic aspect of the present invention relates to the use of the present compounds to reduce the likelihood of acne, baldness, seborrhea or hirsutism.

DETAILED DESCRIPTION OF THE INVENTION

The following terms shall be used throughout the specification to describe the present invention.

The term "patient" is used throughout the specification to describe an animal, preferably a human, to whom treatment, including prophylactic treatment, with the compounds according to the present invention is provided. For treatment of the symptomology, conditions or disease states which are specific for a specific animal such as a human patient, the term patient refers to that specific animal. In most instances in the present invention, the patient is a human with acne, some degree of baldness (including complete baldness) or hirsutism.

The term "effective amount" is used throughout the specification to describe concentrations or amounts of compounds according to the present invention which may be used to produce a favorable change in the symptomology, disease or condition treated, whether that change is a decrease in or reversal of the effects of symptomology or disease state depending upon the disease state or condition treated. In the present invention, in preferred aspects, an effective amount is that amount which is used to treat the condition to be treated, namely acne, baldness, seborrhea or hirsutism. An effective amount for purposes of treating one or more of the above conditions, includes the timing and manner in which an active compound is administered to a patient.

The term "compound" as used in context herein, unless otherwise indicated, refers to any specific chemical compound disclosed herein. Within its use in context, the term generally refers to a single compound, but in certain instances may also refer to stereoisomers and/or optical isomers (including racemic mixtures), as well as specific enantiomers or enantiomerically enriched mixtures of disclosed compounds. The use of the symbol * signifies that the nearest carbon atom to that symbol is a chiral center. Where a chiral center is indicated, the present invention is directed to all configurational isomers about the chiral center, including specific enantiomers and/or racemic (of varying proportion) mixtures of the compounds.

The term "alkyl" is used throughout the specification to describe a hydrocarbon radical containing between one and thirteen carbon units, one and ten carbon units, five and ten carbon units, four and nine carbon units, one and five carbon units, one and four carbon units, one, two, three, four, five, six, seven, eight, nine, ten, eleven, twelve and thirteen. Alkyl groups for use in the present invention include linear, branched-chain groups and cycloalkyl groups such as methyl, ethyl, propyl, i-propyl, butyl, sec-butyl, tert-butyl, pentyl, neo-pentyl, cyclopropyl, cyclobutyl, cyclopentyl, etc. The alkyl groups may be unsubstituted or substituted with $C_1$-$C_3$ alkyl groups.

The term "heterocycle" is used to describe a five- or six-membered ring containing at least one nitrogen group and optionally, up to two more heteroatoms (O, S, N) within the ring. Heterocycles for use in the present invention may include, in certain embodiments and within context, heteroaryls (heterocycles which contain unsaturation). Preferred heterocycles for use in the present invention include piperidine, pyrazine and morpholine, among others.

The term "substituted" is used to describe a substituent on a carbon atom in compounds according to the present invention. In general, in context, a substituent is a halogen group (F, Cl, Br, I) or a $C_1$-$C_3$ alkyl group which itself may be optionally substituted with one or more fluorine groups (e.g., $CF_3$, $CF_2CF_3$).

The term "acne" is used to describe a condition of the skin which results in localized skin inflammation as a result of overactivity of the oil glands at the base of hair follicles. Acne happens when oil (sebaceous) glands come to life around puberty, when these glands are stimulated by male hormones that are produced in the adrenal glands of both boys and girls. The oil glands, which are located just beneath the skin, continuously produce and secrete oil through openings in the skin. The oil lubricates and protects the skin. Under certain circumstances, cells that are close to the openings of the oil glands block the openings. This causes a buildup of oil underneath the skin. Bacteria, omnipresent on the skin, feast on the oil, multiply, and cause the surrounding tissues to become inflamed. If the inflammation is right near the surface, you get a pustule; if it's deeper, a papule (pimple); deeper still and it's a cyst. If the oil breaks though to the surface, the result is a "whitehead". If the oil becomes oxidized (that is, acted on by oxygen in the air), the oil changes from white to black, and the result is a "blackhead."

Compounds according to the present invention may be used to resolve, reduce or control acne. The compounds of the present invention work by reducing sebum (complex mixture of oil, fats and cholesterol which is produced by sebaceous giants) production and/or reducing comedone formation. A comedone is described dermatologically as a plugged pore of sebaceous (oil) and dead skin particles which are stuck in the opening of a hair follicle—these may be whiteheads, blackheads or solar comedones.

The term "baldness" or "alopecia" is used to describe a condition in which hair on the scalp of a man or woman is deficient or non-existent. While the present compounds may be used to treat all forms of loss of hair or baldness, including relatively small areas of hair loss, the present compounds are particularly effective in treating both male and female "pattern baldness".

The term "seborrhea" is used to describe a condition which results in excessively oily skin. It is due to overactive production of sebum (oily material which contains, oils, fats, and cholesterol) from sebaceous glands and can affect both males and females. Although most people with seborrhoea have no other health problems, it is sometimes a sign of underlying Parkinson's disease or acromegaly. In seborrhea, the skin feels unpleasant, and seems to get dirty quickly. The face appears shiny. Make-up may run off or cake. Seborrhoea can also result in acne or seborrhoeic dermatitis.

The term "hirsutism" is used to describe the presence of excessive growth of terminal hair in androgen-dependent areas of a woman's body (including lip, chin, chest, abdomen, or back). It has to be differentiated from hypertrichosis, which is usually familial in nature and associated with an endocrine dysfunction—such as thyroid dysfunction—or with medications such as phenyloin or minoxidil.

Hirsutism may be a sign of a significant medical disorder. Hirsutism is caused by increased androgen action on hair follicles. This may be a result of increased levels of circulating androgens or increased sensitivity of hair follicles to normal serum levels of androgens. Follicles start to develop thick, pigmented hair (terminal hair) as opposed to nonpigmented and thin hair (vellus hair) which is normally seen in these areas.

Causes of hirsutism include excessive production of androgens by the adrenals or ovaries; increased sensitivity of the hair follicles to androgens (which may be caused by exaggerated peripheral 5-α-reductase activity and functional abnormalities in the androgen receptors. Hirsutism is often a source of psychological discomfort as well, and most women who seek treatment for hirsutism do so for cosmetic reasons. It is noted that the present invention is not limited to the treatment of hirsutism only in women—but to men desiring such a cosmetic approach to excessive hair as well.

A preferred therapeutic aspect according to the present invention relates to methods for treating or resolving acne (reducing acne and allowing significant skin clearing), baldness (alopecia—including stimulating hair growth in areas where hair growth has declined or even stopped), seborrhea (reducing sebum production and making skin cosmetically more pleasing) and hirsutism (primarily, but not exclusively in women).

Alternative methods according to the present invention include the administration of effective amounts of one or more compounds according to the present invention to treat or reduce the likelihood of the occurrence or recurrence of acne, baldness, seborrhea and/or hirsutism.

Pharmaceutical compositions based upon these novel chemical compounds comprise the above-described compounds in an effective amount to treat or reduce the likelihood of the occurrence or recurrence of acne, baldness, seborrhea and/or hisutism, optionally in combination with a pharmaceutically acceptable additive, carrier or excipient. Pharmaceutical compositions in topical dosage form for local delivery of the active compounds, in creams, gels and lotions, are preferred. Effective amounts of compounds according to the present invention for use in pharmaceutical dosage form, in particular topical dosage form, in combination with a pharmaceutically acceptable carrier, additive or excipient are contemplated for use in this aspect of the present invention.

Modifications of the active compound can affect the solubility and rate of metabolism of the active species, thus providing control over the delivery of the active species. Further, the modifications may affect the activity of the compound, in some cases increasing the activity over the parent compound. This can easily be assessed by preparing the derivative and testing its activity according to known methods well within the routineer's skill in the art.

The compounds of this invention may be incorporated into formulations for all routes of administration including for example, oral and parenteral including intravenous, intramuscular, intraperitoneal, intrabuccal, transdermal and in suppository form. Topical dosage forms are clearly preferred and include creams, lotions, gels and suppositories which can be delivered to specific sites on the skin to release compounds into the skin to effect the pharmaceutical effect. Compounds of the present invention are preferably used topically as local anti-androgens.

Pharmaceutical compositions based upon these novel chemical compounds comprise the above-described compounds in an effective amount for treating, alleviating and/or resolving the symptomology of the conditions or disease states which have been described hereinabove, especially including acne, baldness, seborrhea and/or hirsutism, optionally in combination with a pharmaceutically acceptable additive, carrier and/or excipient. One of ordinary skill in the art will recognize that an effective amount of one of more compounds according to the present invention will vary with the condition or symptomology to be treated or prevented, its severity, the treatment regimen to be employed, the pharmacokinetics of the agent used, as well as the patient to be treated.

In the pharmaceutical aspect according to the present invention, the compound according to the present invention is formulated preferably in admixture with a pharmaceutically acceptable carrier. In general, it is preferable to administer the pharmaceutical composition in topically administrable form, especially as a cream, lotion, gel, liquid or suppository but other routes of administration may be contemplated in certain instances for example, by parenteral, intravenous, intramuscular, transdermal, buccal, subcutaneous or other route. Of course, one of ordinary skill in the art may modify the formulations within the teachings of the specification to provide numerous formulations for a particular route of administration, if desired, without rendering the compositions of the present invention unstable or compromising their therapeutic activity, noting that the ester groups may be somewhat labile. In particular, the modification of the present compounds to render them more soluble in water or other vehicle, for example, may be accomplished by minor modifications which are well within the ordinary skill in the art. It is also well within the routineer's skill to modify the route of administration and dosage regimen of a particular compound in order to manage the activity and duration of activity of the present compounds for maximum beneficial effect to the patient.

The amount of compound included within therapeutically active formulations according to the present invention is an effective amount for treating the symptom or condition. In its most preferred embodiments, the present compounds are administered topicaly for treating, alleviating or resolving acne, baldness, seborrhea and/or hirsutism or to reduce the likelihood of an occurrence or recurrence of these conditions. In general, a therapeutically effective amount of the presently preferred compound in dosage form usually ranges from slightly less than about 0.0005 mg./kg. to about 0.1 g./kg., preferably about 0.01 mg/kg to about 0.1 mg/kg of the patient or considerably more depending upon the compound used, the condition or symptomology treated and the route of administration, although exceptions to this dosage range may be contemplated by the present invention and are well within the teachings of the present invention. In the specific case of topical formulations applied to a patient's skin, which are the preferred route of administration, the topical dosage falls within the above ranges and are typical dosages (which may be administered once or more times per day) ranging from about 0.01 to about 500 mg. or more of the active, about 0.1 to about 500 mg., about 0.5 to about 250 mg. about 0.5 to about 100 mg, about 1 to about 500 mg, about 0.5 to about 50 mg, about 1 to about 225 mg about 0.25 to about 200 mg, about 0.0125 to about 250 mg, depending upon the activity of the compound, and the size of the area of the skin to which the compounds are to be applied.

To prepare the pharmaceutical compositions according to the present invention, an effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., topical, oral or parenteral, preferably topical. In preparing pharmaceutical compositions in the preferred topical dosage form, any of the usual pharmaceutical media may be used including thickeners, emollients, emulsifiers, etc. may be used to produce creams, gels, salves, ointments and the like for topical delivery to the patient. Alternatively, a patch for transdermal delivery may be used.

In the case of oral dosage forms, liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

The present compounds may be used to treat animals, and in particular, mammals, especially including humans, as patients. Patients may be treated by administering to the patient an effective amount of one or more of the compounds according to the present invention optionally in a pharmaceutically acceptable carrier or diluent, either alone, or in combination with other known pharmaceutical agents, depending upon the condition or symptomology to be treated. This treatment can also be administered in conjunction with other conventional therapies, including the administration of other anti-acne agents and other agents for treatment and/or prophylaxis of alopecia, hirsutism and/or seborrhea.

The active compound is included in the pharmaceutically acceptable carrier or diluent in an amount sufficient to deliver to a patient a therapeutically effective amount for the desired indication, without causing toxic effects in the patient treated.

The compound is conveniently administered in any suitable unit dosage form in an effective amount, including but not limited to one containing less than 1 mg (preferably, at least 1 mg) to 500 mg or more (usually well below the upper range), preferably 5 to 300 mg of active ingredient per unit dosage form. A topical dosage form, including through a transdermal patch ranging from about 1 to about 500 mg, about 5 mg to about 250 mg, about 7.5 mg to about 100 mg, about 1 mg to about 50 mg, or any amount in between any of the above ranges, is usually convenient.

The concentration of active compound in the drug composition will depend on absorption, distribution, inactivation, and excretion rates of the drug as well as other factors known to those of skill in the art. It is to be noted that dosage values will also vary with the severity of the condition or symptomology to be treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time. In its most preferred aspect of the present invention, i.e., in the topical administration of compounds according to the present invention to the patient to be treated, the active may be administered as infrequently as once every several days to several times a day, depending upon the activity of the compounds and other factors well known in the art.

Oral compositions, if used, will generally include an inert diluent or an edible carrier. They may be enclosed in gelatin capsules (soft or hard) or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The active compound may also be administered as a component of an elixir, suspension, syrup, wafer, chewing gum or the like. A syrup may contain, in addition to the active compounds, sucrose and/or corn syrup as a sweetening agent and certain preservatives, dyes and colorings and flavors.

The active compound can also be mixed with other active materials which do not impair the desired action, or with materials which supplement the desired action, such as other hormonal agents, and in other instances depending upon the desired therapy or target, other pharmaceutically active compounds.

Solutions or suspensions primarily used for topical and in some cases, parenteral, intradermal or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. If administered intravenously, preferred carriers include, for example, physiological saline or phosphate buffered saline (PBS). In the case of the preferred pharmaceutical compositions in topical dosage forms, creams, gels and/or viscous lotions may be used as vaginal delivery forms. Creams, gels, lotions and suppositories may be formulated using standing pharmaceutical procedures.

In one embodiment, the active compounds may be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid, among others. Methods for preparation of such formulations are well known and are readily apparent to those skilled in the art.

Liposomal suspensions may also be pharmaceutically acceptable carriers. These may be prepared according to methods known to those skilled in the art. For example, liposome formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

Compounds according to the present invention may be readily prepared using chemical synthetic techniques which are well-known in the art. These syntheses are exemplified in the accompanying text and in the following schemes. Although the presentation is of exemplary chemistry, it is recognized that one of ordinary skill in the art may utilize the teachings of the present invention or modify the procedures otherwise disclosed herein in a manner which enables the routine practice of the present invention. Analogous compounds may be readily synthesized by adapting the specific methodology disclosed and applying well known synthetic organic chemistry techniques well know in the art.

Synthesis of Compounds of General Structure:

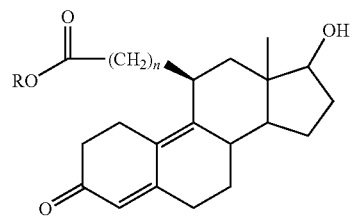

I

The synthesis of the 11β-carboxyalkylene esters, set forth above, is shown in Scheme 1, below, or as derived by analogy from the synthesis in Scheme 1. Other compounds of similar structure may be synthesized by direct analogy using starting materials wherein n is 2 (ethylene) or 3 (propylene). Protection of the phenolic hydroxyl group of 11β-vinyl estradiol (42) as a methyl ether (a) with MeI, $K_2CO_3$ in acetone, followed by protection of the 17β-hydroxyl group (b) as a MOM ether using MOMCI and diisopropylethyl amine in toluene gives the protected steroid 5. Hydroboration/oxidation (c) of the vinyl group of 5 using catechol borane and $LiBH_4$ in THF at rt followed by oxidative work-up with $H_2O_2$—NaOH as we have used in the synthesis of similar 11β-hydroxyethyl substituted steroids (35) gives 6. Oxidation (d) of the terminal alcohol 6 with pyridinium dichromate (PDC) in DMF at rt (43) gives the acid 7. Steroid 7 is then carried through the Birch reduction/double bond isomerization sequence (36) by reduction (e) with Na in liquid $NH_3$, iPrOH and THF to give the diene 8, then the 3-ketone is liberated (f) by stirring with oxalic acid in acetone-water at rt to give 9. Steroid 9 is then (g) brominated and dehydrobrominated with polyvinylpyridinium bromide perbromide, polyvinyl pyridine in pyridine at rt to give the dienone followed by removal of the MOM protecting group (h) using either dimethylboron bromide in $CH_2Cl_2$ (44,45) or pyridinium p-toluenesulfonate in 2-butanone (46) to give 10. Esterification (i) with the appropriate alcohol in the presence of $SOCl_2$ gives 2.

Scheme 1

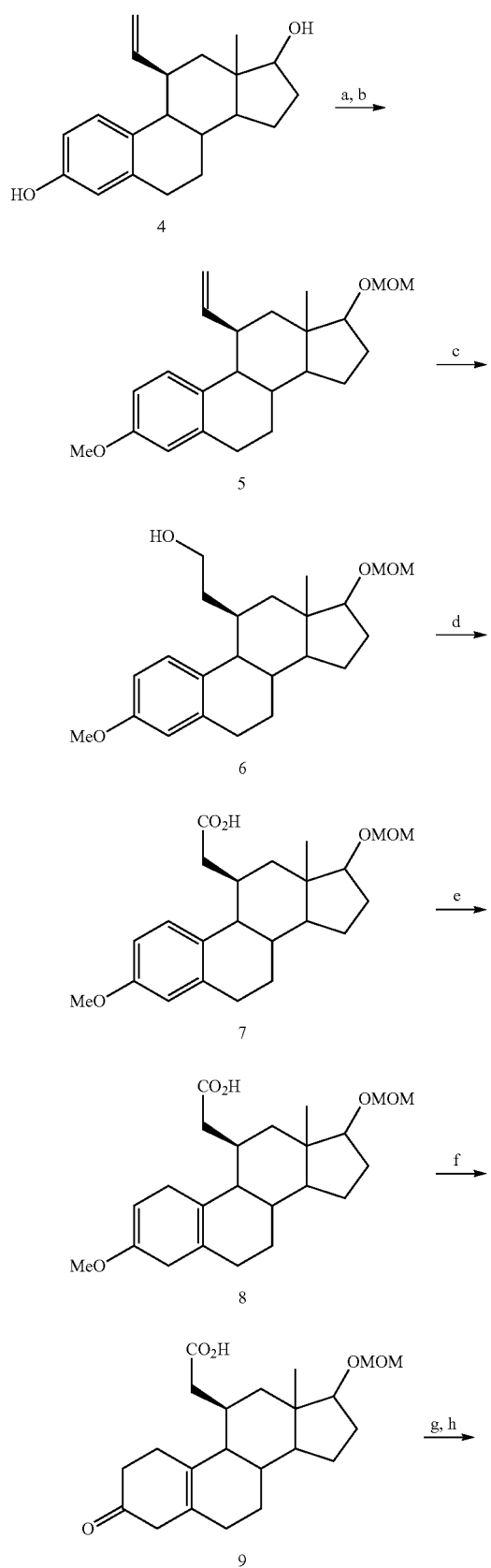

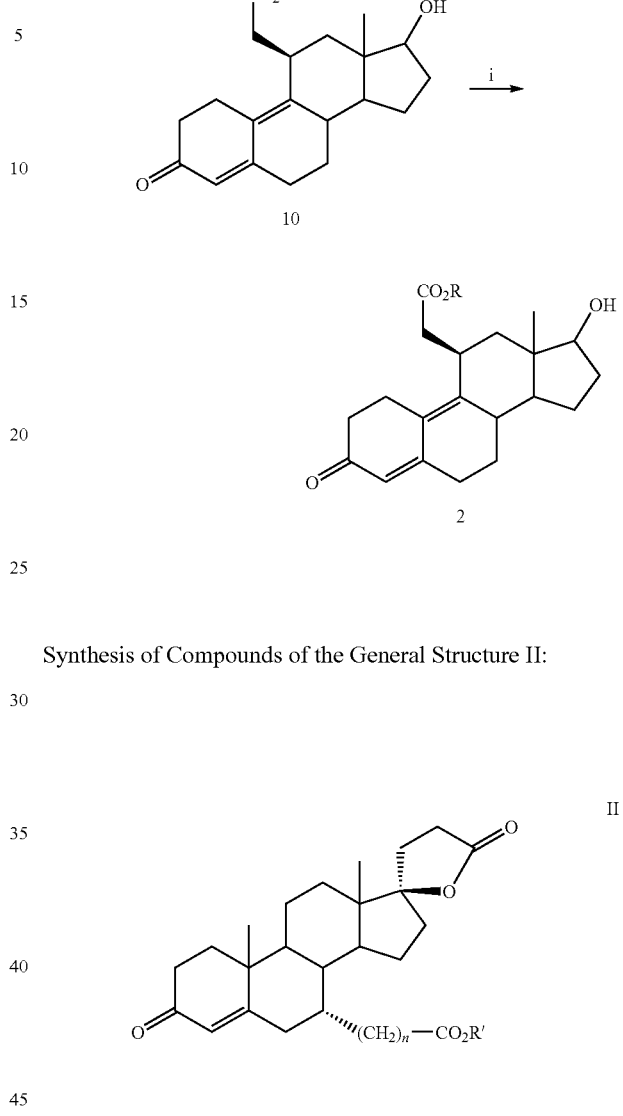

Synthesis of Compounds of the General Structure II:

The synthesis of the 7α-carboxyalkyl steroid esters related to spironolactone, above is shown in Scheme 2, below, and employs the procedure used for the synthesis of the γ-lactone of 17α-carboxyethyl-17α-Δ$^4$-pregnen-17β-ol-3-one-21-carboxylic acid. See, Nedelec, et al., French Patent no. 81-401994 (Roussel-UCLAF). Briefly, copper catalyzed Grignard addition (a) of 1,1-dimethylethoxypropyl magnesium chloride to canrenone in THF at −30° C. gives 28 as the major stereoisomer. Removal of the t-butyl protecting group (b) with HCl-dioxane at rt followed by oxidation (c) of the resulting alcohol with Jones reagent gives 29. Esterification (d) as above gives 27.

Likewise, the same reaction sequence (e, b. c and d) applied to canrenone and 1,1 dimethylethoxyethyl magnesium chloride gives 26. Analogous compounds may be used following the same synthetic steps applied to slightly different starting materials.

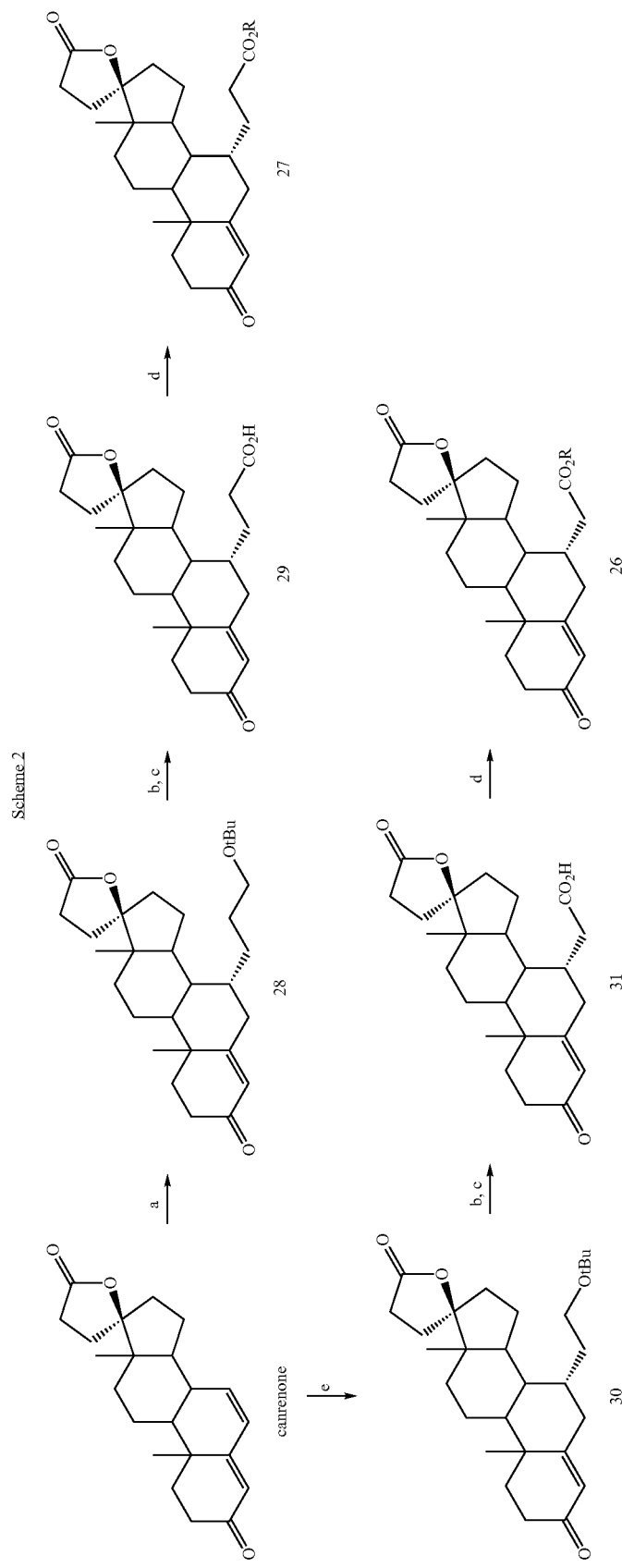
Scheme 2

Synthesis of Compounds of the General Structure III:

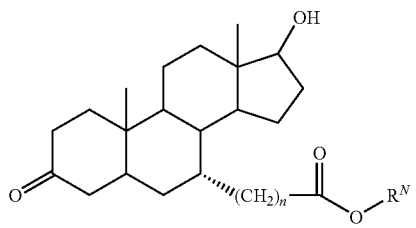

The synthesis of the 7α-substituted steroid 33 (FIG. 10) is shown in Scheme 3, below. The known 7α-allyl steroid 34 (61,62) is subjected to Birch reduction (a) with Li/NH$_3$ (63) then the 3-ketone is protected (b) as the ketal with ethylene glycol and pTsOH in benzene with removal of H$_2$O to give 36. The 17β-hydroxyl group is protected (c) as the MOM ether using MOMCI and diisopropylethyl amine in toluene and the olefin is subjected to the hydroboration/oxidation sequence (d) as above to give 37. The alcohol group of 37 is oxidized (e) with PDC as above to give the acid 38. Steroid 38 is deprotected (f) as above then condensed (g) with 4-hydroxy-1-piperidin-1-yl-butan-1-one (64) in the presence of 2-chloro-1-methypyridinium iodide and triethylamine in CH$_2$Cl$_2$ (65) to give 33. Similar compounds are synthesized by analogy by modifying the starting materials.

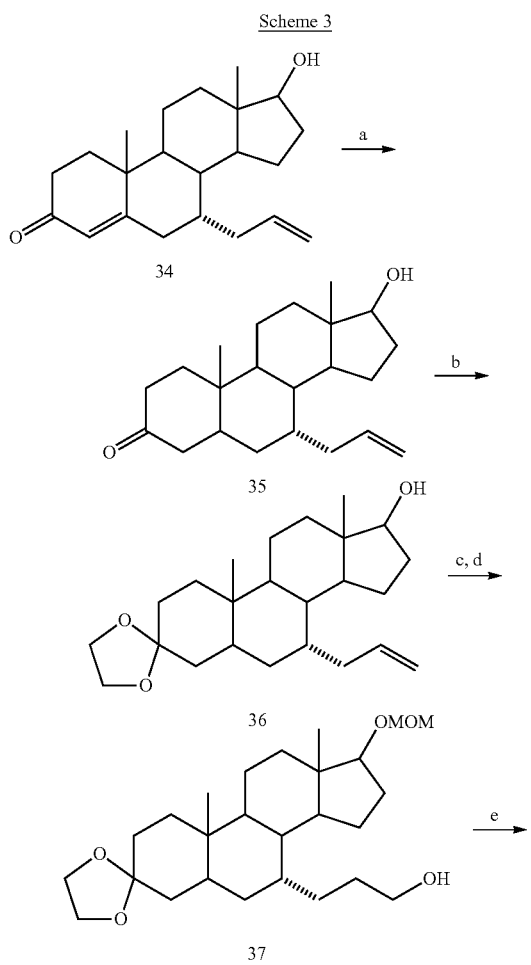

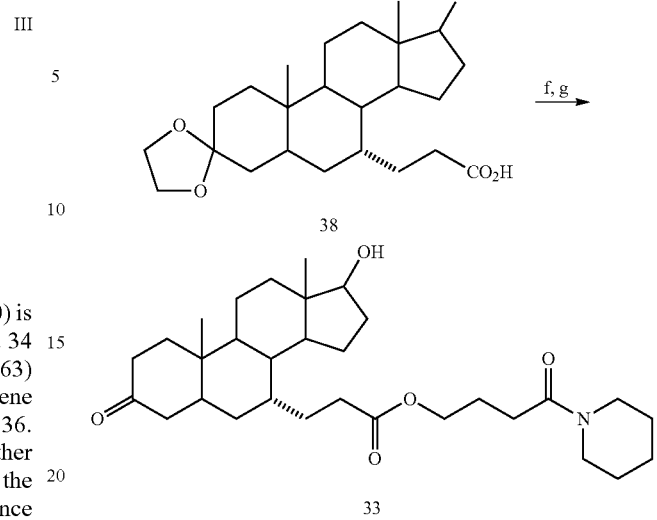

Synthesis of Compounds of the General Structure IV:

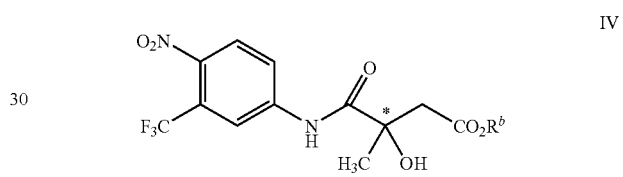

The chiral synthesis of compound 4, above, is shown in Scheme 4, below. For the (S)-enantiomer, the carboxylic acid group of trans-2-phenylcyclohexyl (S)-citramalate 19 (53) is selectively reduced (a) with BH$_3$THF (54) to give the 1,3-diol 20 which is protected (b) as the benzylidene acetal using PHCHO and TsOH at reflux with removal of H$_2$O to give 21. Hydrolysis (c) of 21 using KOH in THF/H$_2$O (53) gives the acid 22 which is coupled (d) with commercially available 4-nitro-3-(trifluoromethyl)aniline at −20° C. (after treatment of 22 with SOCl$_2$ in dimethylacetamide at −20° C.) (49) to give 23. Removal of the protecting group (e) with BCI$_3$ (55) followed by oxidation (f) of the primary alcohol with PDC as above gives 25. Esterification (g) as above gives 18. The (R)-enantiomer may be synthesized by analogy starting from the enantiomeric starting material.

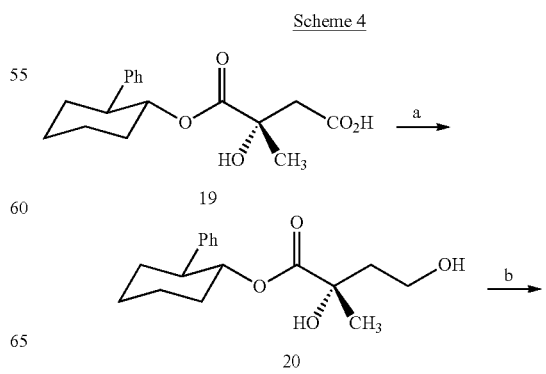

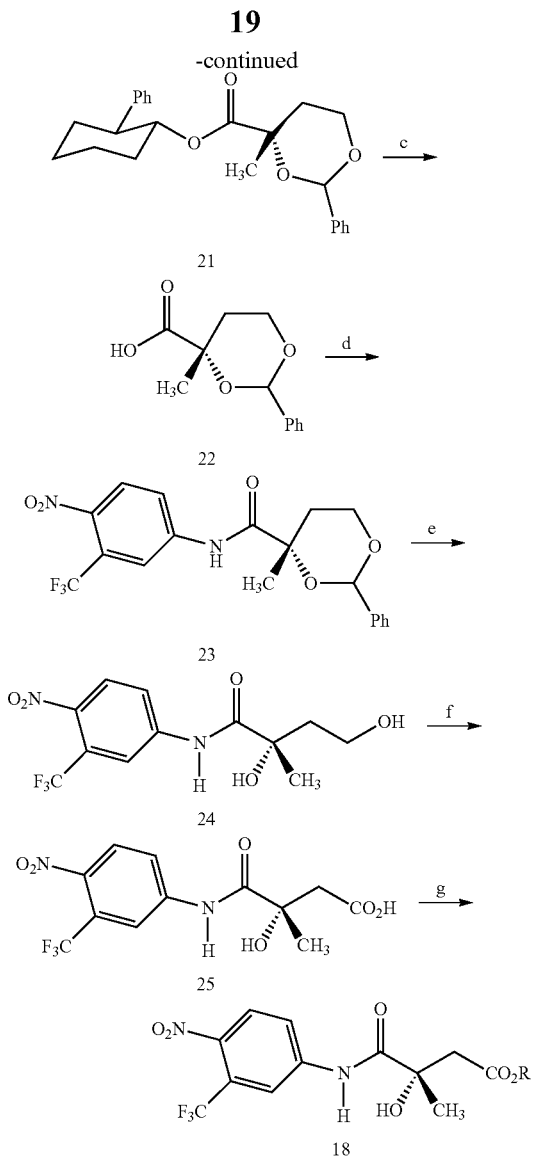

Biological Data/Activity

As part of the testing for biological activity, the esters (preferably, the ethyl ester) and the parent carboxylic acid are tested for binding to the androgen receptor (AR) and for in vitro antiandrogenic activity in the androgen receptor/androgen receptor esterase (AR/ARE) transfected cells (described below). For a good local antiandrogen, the ester must show high affinity for the AR and high antiandrogenic activity, whereas the carboxylic acid parent should be very weak or devoid of these characteristics. One of the strengths of this study is that the rate of hydrolysis can be modified by changing the alcohol portion of the ester, thus if an analog seems have greater systemic actions than we expect, the rate of hydrolysis can be increased, or vice versa. For example, for those esters which exhibit good receptor binding and antiandrogenic activity, while the carboxylic acid is devoid of activity, we synthesize a series of esters, with structural modifications of the alcohol portion of the ester group, designed to either increase or decrease its esterase hydrolysis (for example, the propyl, fluoroethyl ester for increased hydrolysis, and sterically hindered esters, such as the isopropyl and neopentyl esters, or decreased lipophilicity, methyl, for decreased hydrolysis). These esters are tested for their rate of hydrolysis in the hepatic esterase assay (below). These additional esters are tested for AR binding and antiandrogenic activity in the AR/ARE transfected cells. Since the binding assay is performed at 0-2° C., esterase hydrolysis is not a significant factor. However, in the transfected cell assay, enzymatic hydrolysis occurs, and the rate of hydrolysis of the ester group influences biological activity. Thus, after correcting for receptor binding, there is a correlation between biological activity and enzymatic hydrolysis; e.g., compounds with similar receptor binding exhibit different biological activity that correlate with the rate of hydrolysis (ester structure). This correlation will allow us to choose candidates for in vivo testing, for it allows optimization of hydrolysis rate (ester structure) for "local" action. The ester structure can be modified to either decrease the hydrolysis rate in order to maximize local action, or increase hydrolysis rate to minimize systemic action. In the subsequent in vivo assays, the object is to find compounds that show good local antiandrogenic activity, and minimal if any systemic action. The results of these studies identify the initial candidate in each family for in vivo studies. The outcome of this initial study indicates the direction (greater or lesser hydrolysis) that is required, and leads to the appropriate ester for the final clinical entity.

These studies demonstrate the relationship of esterase hydrolysis to biological activity. As can be seen in FIGS. 1 and 2, the ethyl ester 18 (Scheme 4) was less potent compared to casodex than would be predicted on the basis of their AR binding. This apparent discordance between binding and action can be explained by esterase hydrolysis that deactivates 18-ethyl ester but not casodex in the cultured cells. We test this hypothesis by comparing the rate of hydrolysis of specific esters in several cell lines that we have previously transfected with either AR-ARE reporter gene or the ER and ERE. We predict that cells that exhibit the greatest esterase should have the highest casodex/18-ethyl ester ratio of activity, e.g. the lowest activity of the ester analog.

Materials and Methods

In Vitro Biological Testing.

The above-described ester analogs are first screened for antiandrogenic (as well as androgenic) activity by determining their affinity for the AR and for their potency in antagonizing the androgenic stimulation of an androgen responsive reporter gene in cells in culture. In addition, the rate at which these analogs are hydrolyzed by esterase(s) are determined. Potential cross-reaction with other steroid receptor systems (glucocorticoid and mineralocorticoid) are determined because of the spectrum of activity of some of the progenitors (spironolactone and mifepristone): by measuring their binding to mineralocorticoid and glucocorticoid receptors and their inhibition of the action of these receptors in cells transfected with reporter gene constructs.

Androgen Receptor Analysis.

As an initial screening of the test compounds, analysis of binding affinity to AR is determined in cytosol prepared from rat prostates. The androgen binding assay is performed as we have previously described (37, 66, 67). Each non-radioactive test compound are tested over 6 log orders, $10^{-12}$-$10^{-6}$M, and compared with 5a-dihydrotestosterone (DHT), RI881 and known antiandrogens, such as hydroxyflutamide, for competition of the binding of [$^3$H]R1881 (~2 nM) to AR. Prostate glands are obtained from Sprague-Dawley rats that have been castrated 48 hours before sacrifice. The glands are suspended and homogenized in ice-cold TEGDMo buffer (10 mM Tris, 1.5 mM $Na_2$-EDTA, 10% (v/v) glycerol, 1.0 mM dithiothreitol, 25 mM sodium molybdate, pH 7.4 at 4° C.) at 1.5 ml/prostate and centrifuged at 105,000 g for 45 min at 4° C. The supernatant (cytosol) is frozen on dry ice and stored at −80° C.

until assay. For analysis, the cytosol is defrosted on ice, diluted with TEGDMo buffer and incubated with the test analogs overnight on ice. All incubates contain 1 μM triamcinolone acetonide to prevent potential binding to the progesterone receptor. Bound radioligand is separated from free by adsorption with dextran coated charcoal and quantified by counting. Displacement curves are analyzed by a curve-fitting method with the use of the computer program Prism. Typically, each steroid is analyzed in duplicate in 3 separate experiments.

Androgenic or Antiandrogenic Gene Activation.

The synthesized analogs are assayed for androgenic and antiandrogenic activities in a bioassay using cells transfected with the androgen receptor and an androgen responsive reporter gene as previously reported (37, 67). The technique is similar to studies previously performed for antiestrogenic activity in cells transfected with plasmids separately containing ER and an estrogen response element fused to a luciferase reporter gene (34). The rat AR (68) and ARE were obtained from Drs. Centrella and McCarthy at Yale who created the 4XARE-luciferase construct reporter plasmid by cloning four androgen response elements [5'-GGTTCTTGGAGTACT-3'] derived from the rat probasin gene promoter upstream of a minimal RSV promoter (69). COS cells at 50-70% confluence are exposed to 4XARE reporter plasmid at 30 ng per $cm^2$, and to the AR expression plasmid at 10 ng per $cm^2$ in medium supplemented with 0.8% fetal bovine serum for 16 h. The cultures are then supplemented to obtain a final concentration of 5% serum and cultured for a total of 48 h. Afterwards, the cells are treated for 24 h with the analogs alone (agonist) or the analogs+$10^{-9}$M DHT (antagonist). In addition, hydroxyflutamide and spironolactone are run as controls in the agonist and antagonist assays. The analogs are added over a range of $10^{-12}$ to $10^{-6}$M in duplicate and each experiment is replicated in 3 separate experiments. After incubation, the medium is rinsed, lysed and analyzed for reporter gene (luciferase) activity.

The differential between AR binding and the relative antiandrogenic activity as determined in this assay provides initial information and establish trends as to how the ester group should be modified as described above, in the effect of ester modification section, in order to increase or decrease the rate of enzymatic hydrolysis and therefore maximize local antiandrogenic action in vitro.

Esterase Hydrolysis Activity.

The relative rate of hydrolysis of each ester compound, along with the estrogen ester E16-1,2 for comparison, is determined using rat hepatic microsomes under conditions we previously described (32). Liver obtained from Sprague-Dawley rats is washed with phosphate buffered saline and homogenized in 3 volumes of cold 0.25 M sucrose and centrifuged at 700×g for 10 min and then at 10,000×g for 20 min. The resulting supernatant is centrifuged at 105,000×g for 60 min. The resulting pellet is suspended in 0.1 M phosphate buffer pH 7.4 and washed again by centrifugation at 105,000×g for 60 min. The washed pellet is suspended in 0.1 M Tris-HCl pH 8.0 at a concentration of ~13 mg protein/ml and frozen at −80° C. For assay, the pellets are thawed and diluted with the same buffer. The incubation mixture consists of the microsomal enzyme preparation, 0.28 mg protein/ml, the steroid esters, 50 μM, added in 10 μL of ethanol, all in a final volume of 1 mL of Tris buffer pH 8.0. Since we expect the rates of reaction may be widely different for the various esters, the incubation times are varied accordingly to obtain linear kinetics. At several appropriate time points, 100 pL aliquots are withdrawn and the reaction is quenched by extraction with organic solvent (which usually contains a UV absorbing internal standard of similar mobility). The extract is evaporated and analyzed for the esterase-hydrolysis product (the corresponding carboxylic acid) with reversed phase HPLC and UV detection (All of the analogs with exception of the compound 33 absorb strongly in the UV). The hydrolysis of compound 33 are analyzed similarly except that the internal standard are a steroid carboxylate and the hydrolysis product and internal standard are derivatized with N-chloromethyl-4-nitrophthalimide, prior to HPLC and UV detection at 254 nm (70). The UV absorbance is converted to moles of product by comparison to standard curves and corrected for recovery of the internal standard. The velocity of the reaction for each ester, in nmol product/min/ml are normalized to the estrogen ester standard, E1 6-1,2 as relative hydrolytic activity (RHA). All compounds are tested in duplicate in 3 separate experiments.

Esterase Hydrolysis Activity in Transfected Cells in Culture.

We expect that different cell lines transfected with AR/ARE will give different estimates of antiandrogenic potency when the ester containing analogs compared to bicalutamide (casodex) and that this ratio (ester/bicalutamide) are inversely related to the rate of esterase hydrolysis. We will test the relative antiandrogenic potency in cells that we have previously used in double transfections with hormone receptor and their response elements for studying hormone potency, including COS, JAR, SaOS-2, CV1, and rat primary osteoblasts (34,35,37,67). Different levels of esterase activity are likely since these cells are from different tissues and 4 different species (71). The ratio of antiandrogenic potency o the ester analogs to bicalutamide are compared to esterase activity of the cells.

Esterase activity is determined directly kinetically to obtain liner velocity, in transfected cells that are incubated at several intervals up to and including that used for biological (androgenic) activity (usually 6 hours or overnight). The esterase products, the carboxylic acids, are extracted from the media and measured by HPLC as described above in 2c. To obtain sufficient material for accurate measurement, the incubation are modified by increasing the volume to 10 ml and the concentration of ester analog to at least 1 pM to 10 pM. Thus, at the lowest concentration, 1 pM a yield ranging from 10% to 30%, produces 10 to 30 nmoles of product. With the $\Delta^4$-3-ketones, we can accurately detect >0.1 nmole, and the aromatic products about 10 times less. Thus, with this method we can readily measure the products expected in these experiments.

Cross-Reactivity with Other Receptor Systems.

Two of these families of analogs are derived from antihormones that show activity with steroid receptor systems other than the AR system. These include the 7acarboxyalkyl esters, analogs of spironolactone which is also an antimineralocorticoid (72), and the 11 [3-carboxyalkyl esters, loosely based on the antiprogestin/antiglucocorticoid mifepristone. It is unlikely that the 1113-analogs will interact with those receptor systems since the related 11 (i-alkanes do not (36). Since these compounds are designed to act locally, any interaction with these other receptor systems may not be an important issue. Nevertheless, it will provide a broad view of the spectrum of their biological actions.

Mineralocorticoid Receptor.

Binding to the mineralocorticoid are determined as we described (73) by measuring the binding of [$^3$H]aldosterone to MR in kidney cytosol obtained from adrenalectomized rats in the presence of 200 nM RU 28362 (74). Alternatively, $10^4$ M arsenite can be used to eliminate GR binding since it selectively and completely blocks binding to rat GR but not MR (75). Cytosol prepared from adrenalectomized rat kidneys are incubated with 2 nM [$^3$H]aldosterone±200 nM non-radioactive aldosterone+varying concentrations of the analogs over range of concentrations from $10^{-11}$ to $10^{-6}$ M in DMFTEDM buffer for 2 hours at 22° C. DMF-TEDM buffer contains: 50 mM Tris-HCl, 1 mM EDTA, 1.5 mM DTT, 10 mM Na$_2$MoO$_4$, pH 7.5, with the steroid added in 10% DMF (final conc. of DMF=1%). Afterwards, the free steroid is absorbed with charcoal in an ice bath and centrifuged. The supernatant is decanted and the bound steroid is determined by counting (76). The relative binding affinity (RBA) compared to aldosterone is calculated using the computerized curve-fitting program Prism.

Glucocorticoid Receptor:

Binding to GR are determined as we described (76,77) in hepatic cytosol prepared from adrenalectomized rats. [$^3$H] Dexamethasone 2 nM, and varying concentrations, $10^{-11}$ to $10^{-6}$ M of the non-radioactive competing analogs (and dexamethasone, etc) are incubated with cytosol in DMF-TEDM buffer (above) at room temperature for 2 hours (or overnight in an ice bath). Bound steroid is determined in the supernatant fraction after adsorption with charcoal, and the RBA calculated as described above.

Inhibition of Mineralocorticoid Gene Activation.

We will test any of the analogs that bind to the mineralocorticoid receptor for mineralocorticoid or antimineralocorticoid action in cells transfected with the mineralocorticoid receptor and a mineralocorticoid responsive reporter gene. The assay are performed in a manner similar to the procedure above with AR, except transfecting JAR cells with human mineralocorticoid receptor and the mineralocorticoid responsive MMTV-Luc reporter gene as described (78). JAR cells are readily transfected and are chosen since they are devoid of glucocorticoid receptor (79) which avoids spurious results through this receptor system. These plasmid expression vectors have been supplied by Dr. Ron Evans (80). To test for agonistic action, the transfected cells are grown in the presence of a large range of the test analogs alone. Controls are run with aldosterone for comparison. To test for antagonistic action the cells are treated with 1 nM aldosterone plus the test compounds. Positive controls are run with other antagonists such as spironolactone. After incubation, the medium is rinsed, lysed and analyzed for reporter gene (luciferase) activity Inhibition of Glucocorticoid Gene Activation.

Any of the analogs that bind to the glucocorticoid receptor are tested for glucocorticoid and antiglucocorticoid action. Their effect on the stimulation of alkaline phosphatase activity in HeLa cells is also determined. Endogenous alkaline phosphatase activity in the HeLa cell is an excellent marker of glucocorticoid stimulation (81) Furthermore, HeLa cells are devoid of mineralocorticoid receptors (they require transfection with this receptor in order to respond to mineralocorticoids (82)) and thus a response through the mineralocorticoid receptor is avoided. The stimulation of alkaline phosphatase in HeLa cells to develop a 96 well plate assay has been utilized (79). As described, cells are grown for 3 days in the presence of a large dose range of the test analogs alone to determine agonist activity. Controls are run with dexamethasone and cortisol for comparison. To test for antagonist action, the cells are treated with 1 nM dexamethasone plus the test compounds. Positive controls are run with other antagonists such as mifepristone (RU486). Afterwards, the cells are washed, frozen and alkaline phosphatase activity are determined as previously described (83).

In Vivo Local and Systemic Androgenic and Antiandrogenic Action in the Hamster.

Those ester analogs that show the requisite properties for a local antiandrogen (AR binding, antiandrogenic activity in COS cells, hydrolysis by esterase) are tested as antiandrogens in vivo in the Syrian hamster sebaceous gland assay. Androgen sensitive sebaceous glands are located on the inner side of the pinna and they are useful for measuring androgenic and antiandrogenic compounds that are applied directly to the gland (84). Importantly, this assay can be used for measuring systemic as well as local action. The ear pinna to which the test compound is applied serves to determine local activity while the contralateral organ serves to determine systemic action (85). It is apparent that by careful and limited choice of doses any systemic drug could appear to be a local or "soft" drug, e.g. a minimally active dose of an antiandrogen applied directly to the skin where it acts, would not achieve sufficient concentrations in the body to enable it to act systemically. These experiments avoid that type of artifactual "local" effect. Consequently, these compounds are applied over a large dose range, attempting to determine the amount that produces both a local and a systemic effect (if any). The difference in dose level that converts a local into a systemic antiandrogen effect are compared to that of the classic systemic antiandrogen, flutamide, spironolactone, etc.

This assay is performed using the procedure previously described (85) on testosterone treated female hamsters which has the advantage of a consistent androgen background. Ten week old female Syrian hamsters are injected s.c. with 4 pg of testosterone propionate in peanut oil daily. The test antiandrogens (including flutamide and spironolactone) are applied twice daily to the ventral surface of the right ear pinna in 25 pl of acetone for 3 to 4 weeks. Androgenic activity is assayed similarly in animals that are not treated with testosterone propionate. Afterwards, the animals are sacrificed and each ear is cut at the proximal base and the ventral ear skin is manually separated from cartilage. The skin is stained with Sudan Black, washed, and fixed. The specimens are cut sagitally and the size of each sebaceous gland is quantified microscopically using a computerized imaging analysis system.

The results of these studies, coupled with the structural trends obtained in the esterase assay and the antiandrogenic reporter system will provide us with the information needed to synthesize esters (see the effect of ester modification section) that produce optimal "local" activity.

In Vivo Action in the Rat.

Studies on corticoid responses indicate that compounds that show promise in the hamster assay have significant (anti) corticoid activity, and their action in vivo in mineralocorticoid and glucocorticoid is assayed in the rat, the classic model for the study of corticoid action. While there will not be antiandrogen baseline doses in the rat for comparison, nevertheless it will allow us to determine whether these compounds produce anticorticoid effects at very large doses. This assay is performed by first administering the compounds by subcutaneous injection to maximize the effect. Then if active, the analog is applied topically in order to determine the effect of transit through the skin (esterase action).

In Vivo Mineralocorticoid Activity.

Lead compounds tested in the hamster assay that demonstrate binding to the mineralocorticoid receptor and mineralocorticoid or antimineralocorticoid activity in transfected JAR cells are further tested in vivo as described. Sekihara, and Yazaki, *J. Steroid Biochem. Mol. Biol.* 45:235-238, 1993. Twelve week old male rats are bilaterally adrenalectomized and fasted overnight. The next day, the animals are injected intraperitoneally with 3 ml of saline and 0.2 pg aldosterone. In addition, the animals are injected subcutaneously with graded doses of the compounds (a large range whose highest amount exceeds the highest concentration used in the hamster assay above). Those doses that are active are also applied topically (to the shaven backs) in order to determine whether passage through the skin increases the rate of inactivation. Agonist action is determined in animals that do not receive aldosterone. Three hours later the rats are sacrificed and the urine is aspirated from their bladders. The concentration of $Na^+$ and $K^+$ is determined with a flame photometer. Depending upon the assay, $Na^+$ retention are compared to adrenalectomized controls receiving vehicle alone and/or aldosterone. Spironolactone is tested for comparison as a systemic antimineralocorticoid.

In Vivo Glucocorticoid Activity.

Lead compounds in the hamster assay that demonstrate binding to the glucocorticoid receptor and glucocorticoid or antiglucocorticoid activity in transfected HeLa cells are tested in vivo for the induction of tyrosine aminotransferase using the model previously described. Petrazzuoli, et al., *Endocrinology*, 127, 555-559, 1990. Twelve week old male rats are bilaterally adrenalectomized and fasted overnight. The next day, the animals are injected subcutaneously with 2.2 mg of corticosterone (chosen as a weak glucocorticoid), and graded doses of the analogs over a large range (above) administered subcutaneously twice a day. Any doses that are active are also applied topically on the shaven backs in order to determine the effect of transit through the skin. Agonist action is determined in animals that do not receive corticosterone. The animals are sacrificed 12 hours later and the livers are removed, washed, homogenized, centrifuged at 31,000× g. Tyrosine aminotransferase activity are determined in the soluble fraction by monitoring the conversion of p-hydroxyphenylpyruvic acid to p-hyroxybenzaldehyde at 331 nM as described previously. Rosner and Hochberg, *Endocrinology*, 91, 626-632, 1972. Depending upon the assay, enzymatic activity is compared to adrenalectomized controls receiving vehicle alone and/or corticosterone. Mifepristone is tested for comparison as a systemic antiglucocorticoid.

Anti-Hormone Effects in the Fuzzy Rat.

The problem in the rat assay is that it is not possible to interpret the results of the corticoid assays with respect to the antiandrogen assay considering the difference in species (hamster and rat). One likely possibility is that there might be no corticoid activity at all (agonist or antagonist) and then this question is moot. However, if there is slight (anti)corticoid activity at very high doses, then there is a need to compare the corticoid dose to the dose required for "local" antiandrogenic action. This could be accomplished by performing all assays in the "fuzzy" rat (WF/PmWp-"fz"). This rat is a genetic mutant between hairless and hairy albino rats and it is commercially available (Harlan Sprague Dawley). The fuzzy rat is used to study percutaneous absorption of drugs, and it is especially useful as a model of androgen induced acne. Its sebaceous glands are sexually dimorphic; with a normal clear skin in the females; while the males exhibit hyperplastic glandular lobules and their backs contain a thick brown seborrheic coating. This is androgen dependent, reversible by castration and reestablished in the castrate male with testosterone (89). It has been shown in this model that topically applied finasteride, at doses that are locally efficacious, also have a significant systemic effect (prostate) (89). The physiology of the fuzzy rat, including adrenal, appears to be similar to the normal rat (90). This animal has been useful for studying topically applied antiandrogens (89), and it will allow the simultaneous measurement of local (skin), and systemic (prostate) antiandrogen effects along with any anticorticoid (urinary Na+/K+ and hepatic tyrosine aminotransferase) action.

Twenty-five day old fuzzy rats either intact or castrated are treated by the topical administration of various doses (the range are determined in the above experiments) of compounds according to the present invention dissolved in a vehicle of propylene glycol, ethanol and $H_2O$. As described, the analog in 0.5 ml of solution is applied once a day to a 4×4 cm area of the lower, 5 days a week (89). The castrate animals are injected once a day with 200 pg of testosterone in sesame oil. A castrate control group will not be treated with testosterone. For comparison, dose adjusted concentrations of spironolactone will also be administered topically. Animals are housed separately to avoid licking the treated area. After 8 weeks of treatment, the animals are adrenalectomized, and the next day they are treated with either corticosterone or aldosterone as described above, in addition to the antiandrogens. After 3 hours (mineralocorticoid) or 12 hours (glucocorticoid) the animals are sacrificed and the urine analyzed for Na+/K+ and the liver for tyrosine aminotransferase as described above. In a subset, corticoid agonist activity is determined in animals that are administered the test compounds but not injected with either of the corticoids.

For systemic antiandrogen action, the prostate and seminal vesicles are removed and weighed. All of the animals are evaluated for "local" antiandrogenic activity by inhibition the androgen induced sebaceous gland growth as measured by the area of the glandular lobes. Random small skin punch skin samples in the area in which the test compounds were applied, are frozen and 40 pm thick slices are cut horizontal to the epidermal surface (cryostat Leica CM 3050S) and placed in water filled wells. Free floating sections containing the sebaceous glandular lobules are selected and stained with 1% osmium and 2.5% potassium dichromate solution for 2 minutes. After washing with distilled water, the sections are mounted on slides, and the largest of the darkly stained glandular lobules in each glandular image is measured by a computer assisted microimage apparatus (computerized Openlab image analysis system from Improvision, Lexington Mass.) that includes calibration with an ocular micrometer on the microscope for morphometric analysis. (34). All these analyses are performed in a blinded manner. Antiandrogenic compounds produce a large and easily measured decrease in the lobules.

Measurement of Plasma Testosterone.

Conflicting results have indicated that spironolactone may be a steroidogenic inhibitor, specifically acting at 17α-hydroxylase (91), however, this is controversial and many studies have found no effect on levels of plasma testosterone (9,92). While the evidence seems to indicate that there is no effect on androgen synthesis, regardless, given this uncertainty, plasma testosterone is measured in all rats that are not castrated, comparing all rats treated with the test compounds to controls that do not receive the analogs. Serum testosterone are measured by RIA as previously described (93) for male rats by extraction of the serum with ether containing a trace amount of [$^3$H]testosterone as an internal standard. After analysis of the serum, the results are corrected for recovery of the [$^3$H]-internal standard, determined in an aliquot of the extract.

Local Antiandrogen Requirement.

As mentioned above, if a systemic effect is produced with compounds of the present invention, there should be a very large difference between the dose that produces a local antiandrogenic effect on the skin and a systemic effect be it the prostate or contralateral ear pinna. Similarly, for an analog to be particularly useful here, any systemic anticorticoid action must likewise occur only with a dose far exceeding that required for a local antiandrogenic action. In these assays, systemic antiandrogens (spironolactone, flutamide) will also be tested by application to the skin. We define an antiandrogen as locally active or "soft" as one that does not produce a systemic effect or one in which the difference in dose required for local action compared to a systemic action, far exceeds this difference with the classical antiandrogens.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

LITERATURE

1. Bruchovsky N, Wilson J D 1968 The intranuclear binding of testosterone and 5-alpha-androstan-17-beta-ol-3-one by rat prostate. J. Biol. Chem. 243:5953-5960.
2. Imperato-McGinley J, Guerrero L, Gautier T, Peterson R E 1974 Steroid 5alpha-reductase deficiency in man: an inherited form of male pseudohermaphroditism. Science 186:1213-1215.
3. Cleland W H, Mendelson C R, Simpson E R 1985 Effects of aging and obesity on aromatase activity of human adipose cells. J. Clin. Endocrinol. Metab. 60:174-177.
4. Smith E P, Boyd J, Frank G R, Takahashi H, Cohen R M, Specker B, Williams T C, Lubahn D B, Korach K S 1994 Estrogen resistance caused by a mutation in the estrogen-receptor gene in a man. N. Engl. J. Med. 331:1056-1061.
5. Snyder P J 2001 The role of androgens in women. J. Clin. Endocrinol. Metab 86:1006-1007.
6. Speiser P W, New M I 1987 Genotype and hormonal phenotype in nonclassical 21-hydroxylase deficiency. J. Clin. Endocrinol. Metab 64:86-91.
7. Knochenhauer E S, Key T J, Kahsar-Miller M, Waggoner W, Boots L R, Azziz R 1998 Prevalence of the polycystic ovary syndrome in unselected black and white women of the southeastern United States: a prospective study. J. Clin. Endocrinol. Metab 83:3078-3082.
8. Avgerinos P C, Cutler G B, Jr., Tsokos G C, Gold P W, Feuillan P, Gallucci W T, Pillemer S R, Loriaux D L, Chrousos G P 1987 Dissociation between cortisol and adrenal androgen secretion in patients receiving alternate day prednisone therapy. J. Clin. Endocrinol. Metab 65:24-29.
9. Cumming D C, Yang J C, Rebar R W, Yen S S 1982 Treatment of hirsutism with spironolactone. JAMA 247:1295-1298.
10. Cusan L, Dupont A, Gomez J L, Tremblay R R, Labrie F 1994 Comparison of flutamide and spironolactone in the treatment of hirsutism: a randomized controlled trial. Fertil. Steril. 61:281-287.
11. Rittmaster R S 1994 Finasteride. N. Engl. J Med 330:120-125.
12. Thompson I M, Goodman P J, Tangen C M, Lucia M S, Miller G J, Ford L G, Lieber M M, Cespedes R D, Atkins J N, Lippman S M, Carlin S M, Ryan A, Szczepanek C M, Crowley J J, Coltman C A, Jr. 2003 The influence of finasteride on the development of prostate cancer. N. Engl. J Med 349:215-224.
13. McConnell J D, Wilson J D, George F W, Geller J, Pappas F, Stoner E 1992 Finasteride, an inhibitor of 5 alpha-reductase, suppresses prostatic dihydrotestosterone in men with benign prostatic hyperplasia. J. Clin. Endocrinol. Metab 74:505-508.
14. Rosner W 2004 Proscar and propecia—a therapeutic perspective. J. Clin. Endocrinol. Metab. 89:3096-3098.
15. Davis S 1999 Androgen replacement in women: a commentary. J. Clin. Endocrinol. Metab 84:1886-1891.
16. Youngkin E Q 1990 Estrogen replacement therapy and the estraderm transdermal system. Nurse Pract. 15:19-26, 31.
17. Fant R V, Henningfield J E, Shiffman S, Strahs K R, Reitberg D P 2000 A pharmacokinetic crossover study to compare the absorption characteristics of three transdermal nicotine patches. Pharmacol. Biochem. Behav. 67:479-482.
18. Bodor N 1982 Designing safer drugs based on the soft drug approach. Trends Pharmac Sci 3:53-56.
19. Graffner-Nordberg M, Sjodin K, Tunek A, Hallberg A 1998 Synthesis and enzymatic hydrolysis of esters, constituting simple models of soft drugs. Chem Pharm Bull (Tokyo) 46:591-601.

20. Lee H J, Bradlow H L, Moran M C, Sherman M R 1981 Binding of glucocorticoid 21-OIC acids and esters to molybdate-stabilized hepatic receptors. J. Ster. Biochem. 14:1325-1335.
21. Lee H J, Soliman M R I 1982 Anti-inflammatory steroids without pituitary adrenal suppression. Science 215:989-991.
22. Laurent H, Gerhards E, Wiechert R 1975 New biologically active pregnan-21-oic acid esters. J Steroid Biochem 6:185-192.
23. Druzgala P, Hochhaus G, Bodor N 1991 Soft drugs—10. Blanching activity and receptor binding affinity of a new type of glucocorticoid: loteprednol etabonate. J Steroid Biochem Mol Biol 38:149-154.
24. Szelenyi I, Hochhaus G, Heer S, Kusters S, Marx D, Poppe H, Engel J 2000 Loteprednol etabonate: a soft steroid for the treatment of allergic diseases of the airways. Drugs Today (Barc.) 36:313-320.
25. Sarrel P M 1990 Sexuality and Menopause. Obstetrics and Gynecology 75:26 S-30S.
26. Writing Group for the Women's Health Initiative Investigators 2002 Risks and benefits of estrogen plus progestin in healthy postmenopausal women: principal results From the Women's Health Initiative randomized controlled trial. JAMA 288:321-333.
27. Schiff I, Tulchinsky D, Ryan K J 1977 Vaginal absorption of estrone and 1713-estradiol. Fertility and Sterility 28:1063-1066.
28. Rigg L A, Hermann H, Yen S S C 1978 Absorption of estrogens from vaginal creams. N. Engl. J. Med. 298:195-197.
29. Martin P L, Yen S S C, Burnier A M, Hermann H 1979 Systemic absorption and sustained effects of vaginal estrogen creams. JAMA 242:2699-2700.
30. Schiff I, Tulchinsky D, Ryan K J, Kadner S, Levitz M 1980 Plasma estriol and its conjugates following oral and vaginal administration of estriol to postmenopausal women: correlations with gonadotropin levels. Am. J. Obstet. Gynecol. 138:1137-1141.
31. Bucourt R, Vignau M, Torelli V 1978 New biospecific adsorbents for the purification of estradiol receptor. J. Biol. Chem. 253:8221-8228.
32. Labaree D C, Reynolds T Y, Hochberg R B 2001 Estradiol-16a-carboxylic Acid Esters as Locally Active Estrogens. J Med Chem 44:1802-1814.
33. Labaree D C, Zhang J, Harris H A, O'Connor C, Reynolds T Y, Hochberg R B 2003 The Synthesis and Evaluation of B-, C-, and D-ring Substituted Estradiol Carboxylic Acid Esters as Locally Active Estrogens. J Med Chem 46:1886-1904.
34. Zhang J, Labaree D C, Mor G, Hochberg R B 2004 Estrogen to Antiestrogen with a Single Methylene Group Resulting in an Unusual Steroidal SERM. J. Clin. Endocrinol. Metab. 89:3527-3535.
35. Zhang J X, Labaree D C, Hochberg R B 2005 Nonpolar and short sidechain groups at C-11 of estradiol result in antiestrogens. J Med Chem 48:1428-1447.
36. Muddana S S, Price A M, MacBride M M, Peterson B R 2004 1113-Alkyl-49-19-nortestosterone derivatives: high-affinity ligands and potent partial agonists of the androgen receptor. Journal of Medicinal Chemistry 47:4985-4988.
37. Centrella M, McCarthy T L, Wei-Zhong C, Labaree D C, Hochberg R B 2004 Estren (4-Estren-3-a,17(3-diol) Is a prohormone that can regulate estrogen- and androgen-like effects through the androgen receptor. Mol. Endocrinol. 18:1120-1130.
38. He Y, Yin D, Perera M, Kirkovsky L, Stourman N, Li W, Dalton J T, Miller D D 2002 Novel nonsteroidal ligands with high binding affinity and potent functional activity for the androgen receptor. Eur. J Med Chem 37:619-634.
39. Nirde P, Terouanne B, Gallais N, Sultan C, Auzou G 2001 Antimineralocorticoid 11b-substituted spirolactones exhibit androgen receptor agonist activity: a structure function study. Molecular Pharmacology 59:1307-1313.
40. Pannatier A, Testa B, Etter J 1981 Enzymatic hydrolysis by mouse skin homogenates: structure-metabolism relationships of para-nitrobenzoate esters. International Journal of Pharmaceutics 8:167-174.
41. Loozen H J J, Schoonen W G E J 2000 Estrogenic estra-1,3,5(10)-trienes with differential effects on the alpha and beta estrogen receptors, having a linear hydrocarbon of from 5-9 carbon atoms in position 11. Akzo Nobel Patent WO 00/31112:
42. Hanson R N, Napolitano E, Fiaschi R, Onan K D 1990 Synthesis and estrogen receptor binding of novel 1113-substituted estra-1,3,5(10)-triene-3,17(3-diols. J. Med. Chem. 33:3155-3160.
43. Corey E J, Schmidt G 1979 Useful procedures for the oxidation of alcohols involving pyridinium dichromate in aprotic media. Tetrahedron Letters:399-402.
44. Guindon Y, Yoakim C, Morton H E 1983 Cleavage of carbon-oxygen bonds. Dimethylboron bromide. A new reagent for ether cleavage. Tetrahedron Letters 24:2969-2972.
45. Guindon Y, Yoakim C, Morton H E 1984 Dimethylboron bromide and diphenylboron bromide: cleavage of acetals and ketals. J. Org. Chem. 49:3912-3920.
46. Monti H, Leandri G, Klos-Ringuet M, Corriol C 1983 An efficient deprotective method for allylic alcohols protected as methoxyethoxymethyl (MEM) and methoxymethyl (MOM) ethers. Synthetic Communications 13:1021-1026.
47. Sogani P C, Whitmore W F, Jr. 1988 Flutamide and other antiandrogens in the treatment of advanced prostatic carcinoma. Cancer Treat. Res. 39:131-145.
48. Morris J J, Hughes L R, Glen A T, Taylor P J 1991 Non-steroidal antiandrogens. Design of novel compounds based on an infrared study of the dominant conformation and hydrogen-bonding properties of a series of anilide antiandrogens. Journal of Medicinal Chemistry 34:447-455.
49. Tucker H, Crook J W, Chesterson G J 1988 Nonsteroidal antiandrogens. Synthesis and structure-activity relationships of 3-substituted derivatives of 2-hydroxypropionanilides. Journal of Medicinal Chemistry 31:954-959.
50. Yin D, He Y, Perera M A, Hong S S, Marhefka C, Stourman N, Kirkovsky L, Miller D D, Dalton J T 2003 Key structural features of nonsteroidal ligands for binding and activation of the androgen receptor. Molecular Pharmacology 63:211-223.
51. Seligson A L, Campion B K, Brown J W, Terry R C, Kucerova R, Bienova M, Hajduch M, Sovak M 2003 Development of fluridil, a topical suppressor of the androgen receptor in androgenetic alopecia. Drug Dev. Res. 59:292-306.
52. Poujol N, Wurtz J M, Tahiri B, Lumbroso S, Nicolas J C, Moras D, Sultan C 2000 Specific recognition of androgens by their nuclear receptor. A structure-function study. J. Biol. Chem. 275:24022-24031.
53. Whitesell J K, Nabona K, Deyo D 1989 Observations on the reactions of chiral pyruvates. Synthesis of (−)- and (+)-citramalic acid. J. Org. Chem. 54:2258-2260.
54. Wuensch B, Diekmann H, Hoefner G 1993 Homochiral 2,4-disubstituted 1,3-dioxanes from (S)-(−)-malic acid:

stereoselective synthesis and investigation of the NMDA receptor affinity of all four stereoisomers. Liebigs Annalen der Chemie: 1273-1278.
55. Bonher T G, Bourne E J, McNally S 1960 Dealkylation and deacylation of carbohydrate derivatives with boron trichloride and boron tribromide. Journal of the Chemical Society, Abstracts: 2929-2934.
56. Steelman S L, Brooks J R, Morgan E R, Patanelli D J 1969 Anti-androgenic activity of spironolactone. Steroids 14:449-450.
57. Sobbrio G A, Granata A, Panacea A, Trimarchi F 1989 Effectiveness of short term canrenone treatment in idiopathic hirsutism. Minerva Endocrinol. 14:105-108.
58. Cutler G B, Jr., Sauer M A, Loriaux D L 1979 SC 25152: a potent mineralocorticoid antagonist with decreased antiandrogenic activity relative to spironolactone. J. Pharmacol. Exp. Ther. 209:144-146.
59. Nedelec L, Torelli V, Philibert D 1983 3-Oxo-4-unsaturated. or 1,4-unsaturated steroid derivatives substituted at position seven, their utilization as pharmaceutical compositions and compositions containing them. (Roussel-UCLAF, Fr. Patent 81-401994:
60. Kaiho S, Ohizumi I, Tamura K, Kato N, Yoneya T, Tachibana K 20010301 Preparation of androstane derivatives as antiandrogen agents. (Chugai Seiyaku Kabushiki Kaisha, Japan Patent 2000-J P5636:
61. Nickisch K, Laurent H 1988 Stereoselective synthesis of 7a-allyl- and 7a-propylsteroids. Tetrahedron Letters 29:1533-1536.
62. Solo A J, Caroli C, Darby M V, McKaya T, Slaunwhite W D, Hebborn P 1982 7a-Alkyltestosterone derivatives: synthesis and activity as androgens and as aromatase inhibitors. Steroids 40:603-614.
63. Choe Y S, Lidstrom P J, Chi D Y, Bonasera T A, Welch M J, Katzenellenbogen J A 1995 Synthesis of 11 [3-[18F]fluoro-5a-dihydrotestosterone and 11 [3-[18F]fluoro-19-nor-5a-dihydrotestosterone: Preparation via halofluorination-reduction, receptor binding, and tissue distribution. J. Med. Chem. 38:816-825.
64. Wang W B, Roskamp E J 1992 Tin(11) amides: new reagents for the conversion of esters to amides. J. Org. Chem. 57:6101-6103.
65. Mukaiyama T, Usui M, Shimada E, Saigo K 1975 Convenient method for the synthesis of carboxylic esters. Chemistry Letters: 1045-1048.
66. Hoyte R M, Borderon K, Bryson K, Allen R, Hochberg R B, Brown T J 1994 Synthesis and evaluation of 7a-Iodo-5a-dihydrotestosterone as a potential radioligand for androgen receptor. J. Med. Chem. 37:1224-1230.
67. Labaree D C, Hoyte R M, Nazareth L V, Weigel N L, Hochberg R B 1999 7a-iodo and fluoro steroids as androgen receptor mediated imaging agents. J. Med. Chem. 42:2021-2034.
68. Chang C S, Kokontis J, Liao S T 1988 Molecular cloning of human and rat complementary DNA encoding androgen receptors. Science 240:324-326.
69. McCarthy T L, Chang W Z, Liu Y, Centrella M 2003 Runx2 integrates estrogen activity in osteoblasts. J. Biol. Chem. 278:43121-43129.
70. Lindner W 1980 N-chloromethyl-4-nitrophthalimide as derivatization reagents for high-performance liquid chromatography. Journal of Chromatography 198:367-372.
71. Lund-Pero M, Jeppson B, Arneklo-Nobin B, Sjogren H-O, Holmgren K, Pero R W 1994 Nonspecific steroidal esterase activity and distribution in human and other mammalian tissues. Clinica Chimica Acta 224:9-20.
72. Corvol P, Claire M, Oblin M E, Geering K, Rossier B 1981 Mechanism of the antimineralocorticoid effects of spirolactones. Kidney Int. 20:1-6.
73. Brown T J, MacLusk r N J, Toran-Allerand C D, Zielinski J E, Hochberg R B 1989 Characterization of 11 [3-methoxy-16a-['51]iodoestradiol binding: neuronal localization of estrogen binding sites in the developing rat brain. Endocrinology 124:2074-2088.
74. Moguilewsky M, Raynaud J P 1980 Evidence for a specific mineralocorticoid receptor in rat pituitary and brain. J. Steroid Biochem. 12:309-314.
75. Lopez S, Miyashita Y, Simons S S, Jr. 1990 Structurally based, selective interaction of arsenite with steroid receptors. J. Biol. Chem. 265:16039-16042.
76. Hoyte R M, Labaree D C, Fede J M, Harris C, Hochberg R B 1998 Iodinated and fluorinated steroid 2'-aryl-[3,2-c]pyrazoles as potential glucocorticoid receptor imaging agents. Steroids 63:595-602.
77. Petrazzuoli M, Pahuja S L, Lanier J M, Hochberg R B 1990 Biological activity of the fatty acid ester metabolites of corticoids. Endocrinology 127:555-559.
78. Quinkler M, Meyer B, Bumke-Vogt C, Grossmann C, Gruber U, Oelkers W, Diederich S, Bahr V 2002 Agonistic and antagonistic properties of progesterone metabolites at the human mineralocorticoid receptor. Eur. J Endocrinol. 146:789-799.
79. Chambers S K, Ivins C M, Kacinski B M, Hochberg R B 2004 An unexpected effect of glucocorticoids on stimulation of c-fms proto-oncogene expression in choriocarcinoma cells expressing little glucocorticoid receptor. Am J Obstet Gynecol 190:974-985.
80. Arriza J L, Weinberger C, Cerelli G, Glaser T M, Handelin B L, Housman D E, Evans R M 1987 Cloning of human mineralocorticoid receptor complementary DNA: Structural and functional kinship with the glucocorticoid receptor. Science 237:268-275.
81. Littlefield B A, Cidlowski N B, Cidlowski J A 1980 Modulation of glucocorticoid effects and steroid receptor binding in butyrate-treated HeLa S3 cells. Arch. Biochem. Biophys. 201:174-184.
82. Jausons-Loffreda N, Balaguer P, Auzou G, Pons M 1994 Development of specific bioluminescent in vitro assays for selecting potential antimineralocorticoids. J Steroid Biochem. Mol. Biol. 49:31-38.
83. Littlefield B A, Gurpide E, Markiewicz L, McKinley B, Hochberg R B 1990 A simple and sensitive microtiter plate estrogen bioassay based on stimulation of alkaline phosphatase in Ishikawa cells: Estrogenic action of A5 adrenal steroids. Endocrinology 127:2757-2762.
84. Luderschmidt C, Eiermann W, Jawny J, Bidlingmaier F, Ring J 1984 17 alpha-Propylmesterolone (SH 434): an antiandrogenic sebosuppressive substance not influencing circulating testosterone concentrations. Experimental studies in Syrian hamsters. Naunyn Schmiedebergs Arch. Pharmacol. 328:214-218.
85. Matias J R, Malloy V L, Orentreich N 1988 Synergistic antiandrogenic effects of topical combinations of 5 alpha-reductase and androgen receptor inhibitors in the hamster sebaceous glands. J Invest Dermatol. 91:429-433.
86. Gaunt R, Gisoldi E, Smith N 1971 Refractoriness to renal effects of aldosterone in the golden hamster. Endocrinology 89:63-69.
87. Sekihara H, Yazaki Y 1993 5 alpha-Dihydro-11-deoxycorticosterone as a mineralocorticoid agonist and antagonist: evidence for a weak mineralocorticoid as an antagonist of potent mineralocorticoids. J Steroid Biochem. Mol. Biol. 45:235-238.

88. Rosner W, Hochberg R B 1972 Corticosteroid-binding globulin in the rat: Isolation and studies of its influence on cortisol action in vivo. Endocrinology 91:626-632.
89. Ye F, Imamura K, Imanishi N, Rhodes L, Uno H 1997 Effects of topical antiandrogen and 5-alpha-reductase inhibitors on sebaceous glands in male fuzzy rats. Skin Pharmacol. 10:288-297.
90. Marit G B, Young S M, Hadick C L 1995 Anatomic and physiologic characterization of the WF/PmWp-"fz" (fuzzy) rat. Lab Anim Sci 45:184-190.
91. Menard R H, Guenthner T M, Kon H, Gillette J R 1979 Studies on the destruction of adrenal and testicular cytochrome P-450 by spironolactone. Requirement for the 7alpha-thio group and evidence for the loss of the heme and apoproteins of cytochrome P-450. J. Biol. Chem. 254: 1726-1733.
92. Rey F O, Valterio C, Locatelli L, Ramelet A A, Felber J P 1988 Lack of endocrine systemic side effects after topical application of spironolactone in man. J. Endocrinol. Invest 11:273-278.
93. Borg W, Shackleton C H L, Pahuja S L, Hochberg R B 1995 Endogenous Long-Lived Esters of Testosterone in the Rat. Proc. Natl. Acad. Sci. USA 92:1545-1549.

The invention claimed is:

1. A compound according to the chemical structure:

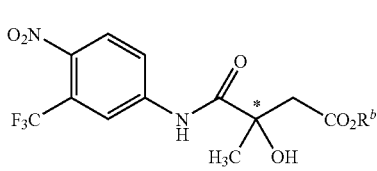

IV wherein $R^b$ is an optionally substituted $C_1$-$C_6$ alkyl group.

2. The compound according to claim 1, wherein $R^b$ is an optionally substituted $C_2$ or $C_3$ alkyl group.

3. The compound according to claim 1 which is

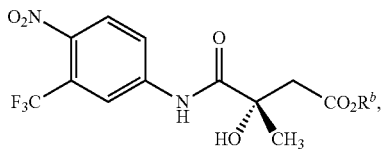

wherein $R^b$ is an ethyl group.

4. A pharmaceutical composition comprising an effective amount of a compound according to claim 1 in combination with a pharmaceutically acceptable carrier, additive or excipient.

5. A pharmaceutical composition comprising an effective amount of a compound according to claim 2 in combination with a pharmaceutically acceptable carrier, additive or excipient.

6. A pharmaceutical composition comprising an effective amount of a compound according to claim 3 in combination with a pharmaceutically acceptable carrier, additive or excipient.

7. The composition according to claim 4 in topical dosage form.

8. The composition according to claim 5 in topical dosage form.

9. The composition according to claim 6 in topical dosage form.

10. A method of treating acne in a patient in need thereof comprising administering an effective amount of a composition according to claim 4 to said patient.

11. A method of treating acne in a patient in need thereof comprising administering an effective amount of a composition according to claim 7 to said patient.

12. A method of treating acne in a patient in need thereof comprising administering an effective amount of a composition according to claim 8 to said patient.

13. A method of treating acne in a patient in need thereof comprising administering an effective amount of a composition according to claim 9 to said patient.

14. A method of treating baldness in a patient in need thereof comprising administering an effective amount of a composition according to claim 4 to said patient.

15. A method of treating baldness in a patient in need thereof comprising administering an effective amount of a composition according to claim 7 to said patient.

16. A method of treating baldness in a patient in need thereof comprising administering an effective amount of a composition according to claim 8 to said patient.

17. A method of treating baldness in a patient in need thereof comprising administering an effective amount of a composition according to claim 9 to said patient.

18. The method according to claim 14 wherein said baldness is female pattern baldness.

19. The method according to claim 15 wherein said baldness is female pattern baldness.

20. The method according to claim 16 wherein said baldness is female pattern baldness.

21. The method according to claim 17 wherein said baldness is female pattern baldness.

22. The method according to claim 14 wherein said baldness is male pattern baldness.

23. The method according to claim 15 wherein said baldness is male pattern baldness.

24. The method according to claim 16 wherein said baldness is male pattern baldness.

25. The method according to claim 17 wherein said baldness is male pattern baldness.

26. A method of treating hirsutism in a patient in need thereof comprising administering an effective amount of a composition according to claim 4 to said patient.

27. A method of treating hirsutism in a patient in need thereof comprising administering an effective amount of a composition according to claim 7 to said patient.

28. A method of treating hirsutism in a patient in need thereof comprising administering an effective amount of a composition according to claim 8 to said patient.

29. A method of treating hirsutism in a patient in need thereof comprising administering an effective amount of a composition according to claim 9 to said patient.

30. The method according to claim 26 wherein said patient is a female.

31. The method according to claim 27 wherein said patient is a female.

32. The method according to claim 28 wherein said patient is a female.

33. The method according to claim 29 wherein said patient is a female.

34. A method of treating seborrhea in a patient in need thereof comprising administering an effective amount of a composition according to claim 4 to said patient.

35. A method of treating seborrhea in a patient in need thereof comprising administering an effective amount of a composition according to claim 7 to said patient.

36. A method of treating seborrhea in a patient in need thereof comprising administering an effective amount of a composition according to claim 8 to said patient.

37. A method of treating seborrhea in a patient in need thereof comprising administering an effective amount of a composition according to claim 9 to said patient.

* * * * *